(12) United States Patent
Malofsky et al.

(10) Patent No.: US 9,221,739 B2
(45) Date of Patent: Dec. 29, 2015

(54) METHYLENE BETA-DIKETONE MONOMERS, METHODS FOR MAKING METHYLENE BETA-DIKETONE MONOMERS, POLYMERIZABLE COMPOSITIONS AND PRODUCTS FORMED THEREFROM

(71) Applicant: Sirrus, Inc., Loveland, OH (US)

(72) Inventors: Adam G. Malofsky, Loveland, OH (US); Jeffrey M. Sullivan, Goshen, OH (US); Tanmoy Dey, Willington, CT (US); Bernard M. Malofsky, Bloomfield, CT (US)

(73) Assignee: SIRRUS, INC., Loveland, OH (US)

( * ) Notice: Subject to any disclaimer, the term of this patent is extended or adjusted under 35 U.S.C. 154(b) by 0 days.

(21) Appl. No.: 14/352,369

(22) PCT Filed: Oct. 18, 2012

(86) PCT No.: PCT/US2012/060840
§ 371 (c)(1),
(2) Date: Apr. 17, 2014

(87) PCT Pub. No.: WO2013/059479
PCT Pub. Date: Apr. 25, 2013

(65) Prior Publication Data
US 2014/0275400 A1    Sep. 18, 2014

Related U.S. Application Data

(60) Provisional application No. 61/549,152, filed on Oct. 19, 2011, provisional application No. 61/549,104, filed on Oct. 19, 2011, provisional application No. 61/549,092, filed on Oct. 19, 2011.

(51) Int. Cl.
| | | |
|---|---|---|
| *C07C 45/00* | (2006.01) |
| *C07C 49/00* | (2006.01) |
| *C08L 27/12* | (2006.01) |
| *B03D 1/016* | (2006.01) |
| *C08F 214/06* | (2006.01) |
| *C08L 27/00* | (2006.01) |
| *C07C 67/03* | (2006.01) |
| *C09J 133/06* | (2006.01) |
| *C07C 45/75* | (2006.01) |
| *C07C 49/794* | (2006.01) |
| *C07C 49/796* | (2006.01) |
| *C07C 49/798* | (2006.01) |
| *C07C 49/80* | (2006.01) |
| *C07D 307/46* | (2006.01) |
| *C07D 333/22* | (2006.01) |
| *C08F 116/36* | (2006.01) |
| *C08F 128/06* | (2006.01) |
| *C09D 129/12* | (2006.01) |

(Continued)

(52) U.S. Cl.
CPC ............. *C07C 67/03* (2013.01); *C07C 45/75* (2013.01); *C07C 49/794* (2013.01); *C07C 49/796* (2013.01); *C07C 49/798* (2013.01); *C07C 49/80* (2013.01); *C07C 67/30* (2013.01); *C07C 69/604* (2013.01); *C07C 69/738* (2013.01); *C07D 307/46* (2013.01); *C07D 307/54* (2013.01); *C07D 333/22* (2013.01); *C07D 333/24* (2013.01); *C08F 20/28* (2013.01); *C08F 20/68* (2013.01); *C08F 24/00* (2013.01); *C08F 28/06* (2013.01); *C08F 116/36* (2013.01); *C08F 128/06* (2013.01); *C08F 222/14* (2013.01); *C09D 129/12* (2013.01); *C09D 141/00* (2013.01); *C09J 133/06* (2013.01); *C08F 222/1006* (2013.01)

(58) Field of Classification Search
None
See application file for complete search history.

(56) References Cited

U.S. PATENT DOCUMENTS

| | | | |
|---|---|---|---|
| 2,277,479 A | 3/1942 | D'Alelio |
| 2,313,501 A | 3/1943 | Bachman |

(Continued)

FOREIGN PATENT DOCUMENTS

| | | | |
|---|---|---|---|
| GB | 432628 A | 7/1935 |
| JP | 2-281013 | * 11/1990 |

(Continued)

OTHER PUBLICATIONS

NPL Yamauchi et al. Tetrahedron Asymetry 12, (2001), 3113-3118.*

(Continued)

*Primary Examiner* — Susannah Chung
*Assistant Examiner* — Robert T Butcher
(74) *Attorney, Agent, or Firm* — The Dobrusin Law Firm, P.C.

(57) ABSTRACT

The present invention provides methylene beta-diketone monomers, methods for producing the same, and compositions and products formed therefrom. In the method for producing the methylene beta-diketones of the invention, a beta-diketone is reacted with a source of formaldehyde in a modified Knoevenagel reaction optionally in the presence of an acidic or basic catalyst, and optionally in the presence of an acidic or non-acidic solvent, to form reaction complex. The reaction complex may be an oligomeric complex. The reaction complex is subjected to further processing, which may be vaporization by contact with an energy transfer means in order to isolate the beta-diketone monomer. The present invention further compositions and products formed from methylene beta-diketone monomers of the invention, including monomer-based products (e.g., inks, adhesives, coatings, sealants or reactive molding) and polymer-based products (e.g., fibers, films, sheets, medical polymers, composite polymers and surfactants).

16 Claims, 9 Drawing Sheets

(51) Int. Cl.

| | |
|---|---|
| C09D 141/00 | (2006.01) |
| C07C 67/30 | (2006.01) |
| C07C 69/738 | (2006.01) |
| C07D 307/54 | (2006.01) |
| C07D 333/24 | (2006.01) |
| C08F 20/28 | (2006.01) |
| C08F 20/68 | (2006.01) |
| C08F 24/00 | (2006.01) |
| C08F 28/06 | (2006.01) |
| C07C 69/604 | (2006.01) |
| C08F 222/14 | (2006.01) |
| C08F 222/10 | (2006.01) |

(56) References Cited

U.S. PATENT DOCUMENTS

| | | |
|---|---|---|
| 2,330,033 A | 9/1943 | D'Alello |
| 3,042,710 A | 7/1962 | Dickstein |
| 3,197,318 A | 7/1965 | Halpern |
| 3,221,745 A | 12/1965 | Coover, Jr. |
| 3,523,097 A | 8/1970 | Coover, Jr. |
| 3,557,185 A | 1/1971 | Ito |
| 3,758,550 A | 9/1973 | Eck et al. |
| 3,936,486 A | 2/1976 | Egger et al. |
| 3,975,422 A | 8/1976 | Buck |
| 3,995,489 A | 12/1976 | Smith et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,102,809 A | 7/1978 | Smith et al. |
| 4,105,688 A | 8/1978 | Arni et al. |
| 4,154,914 A | 5/1979 | Kuraya |
| 4,160,864 A | 7/1979 | Ponticello et al. |
| 4,198,334 A | 4/1980 | Rasberger |
| 4,237,297 A | 12/1980 | Rody et al. |
| 4,256,908 A | 3/1981 | Nishimura et al. |
| 4,329,479 A | 5/1982 | Yabutani et al. |
| 4,399,300 A | 8/1983 | Prange et al. |
| 4,444,928 A | 4/1984 | Karrer |
| 4,504,658 A | 3/1985 | Narisada et al. |
| 4,517,105 A | 5/1985 | Laemmle et al. |
| 4,556,649 A | 12/1985 | Salzburg et al. |
| 4,578,503 A | 3/1986 | Ishikawa et al. |
| 4,698,333 A | 10/1987 | Fauss et al. |
| 4,727,701 A | 3/1988 | Figari |
| 4,736,056 A | 4/1988 | Smith et al. |
| 4,835,153 A | 5/1989 | Kabota et al. |
| 4,914,226 A | 4/1990 | Di Trapani et al. |
| 4,931,584 A | 6/1990 | Bru-Magniez et al. |
| 5,021,486 A | 6/1991 | Galbo |
| 5,039,720 A | 8/1991 | Saatweber et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,259,835 A | 11/1993 | Clark et al. |
| 5,292,937 A | 3/1994 | Manning et al. |
| 5,312,864 A | 5/1994 | Wenz et al. |
| 5,334,747 A | 8/1994 | Steffen |
| 5,426,203 A | 6/1995 | Sohn et al. |
| 5,514,371 A | 5/1996 | Leung et al. |
| 5,514,372 A | 5/1996 | Leung et al. |
| 5,550,172 A | 8/1996 | Regula et al. |
| 5,575,997 A | 11/1996 | Leung et al. |
| 5,582,834 A | 12/1996 | Leung et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 6,106,807 A | 8/2000 | Albayrak et al. |
| 6,211,273 B1 | 4/2001 | Bru-Magniez et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,395,737 B1 | 5/2002 | Defossa et al. |
| 6,395,931 B1 | 5/2002 | Carvalho et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,750,298 B1 | 6/2004 | Bru-Magniez et al. |
| 6,794,365 B2 | 9/2004 | Al-Obeidi et al. |
| 7,109,369 B2 | 9/2006 | Nose et al. |
| 7,208,621 B2 | 4/2007 | Nose et al. |
| 7,553,989 B2 | 6/2009 | Sawabe et al. |
| 7,659,423 B1 | 2/2010 | McArdle |
| 7,663,000 B2 | 2/2010 | Dekkers et al. |
| 2004/0076601 A1 | 4/2004 | Bru-Magniez et al. |
| 2004/0220060 A1 | 11/2004 | Bartley et al. |
| 2007/0049655 A1 | 3/2007 | Yoshimune et al. |
| 2010/0286433 A1 | 11/2010 | Malofsky et al. |
| 2010/0286438 A1 | 11/2010 | Malofsky et al. |
| 2011/0015406 A1 | 1/2011 | Umetani et al. |
| 2011/0024392 A1 | 2/2011 | Sato et al. |
| 2011/0164322 A1 | 7/2011 | Morozumi et al. |

FOREIGN PATENT DOCUMENTS

| | | |
|---|---|---|
| WO | WO-2007/120630 A2 | 10/2007 |
| WO | WO-2011/059104 A1 | 5/2011 |
| WO | WO-2012/054633 A2 | 4/2012 |
| WO | WO-2012054616 A2 | 4/2012 |

OTHER PUBLICATIONS

Valentine G. Nenajdenko et al, Reaction of 2-Methylene-1,3-dicarbonyl Compounds Containing a CF3-Group with 1,3-Dienes Tetrahedron 56 (2000) 6549-6556.*

K. Okamura and T. Date, A Facile Conversion of Ethoxydihydropyrans to 4-Cyanoethylisoxazoles, J. Heterocyclic Chem. 33, 383 (1996).*

Translation JP 2-281013 Endo, Takeshi, Kishimoto, Masaaki, Diketone Compound-Based Copolymer, Nov. 16, 1990, p. 1-11.*

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol, 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl gloiosiphne A by Way of Palladium-Catalyzed Domino Cyclization," T. Org <http://T.Org>. Chem., (2007), vol. 72, pp. 3667-3671.

H. Jung et al,: "New and General Methods for the Synthesis of Arylmethylene Bis(3-Hydroxy-2-Cyclohexene-1-Ones) and Xanthenediones by EDDA and In(OTf)3-Catalyzed One-Pot

(56) References Cited

OTHER PUBLICATIONS

Domino Knoevenagel/Michael or Koevenagel/Michael/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer, (1998), vol. 39, No. I, pp. 173-181.

C.Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a.

P, Ballesteros et al.: "Dl-*tert*-Butyl Methylenemalonate [Propanedioic Acid, Methylene-, bis(1,1-dimethylethyl)ester]," Organic Syntheses. Coll. (1990), vol. 7, p. 142 ; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes ; via the Knoevenagel Condensation," Tetrahedron Letters, (2002), vol. 43, pp. 1127-1130.

P. Ballesteros et al.: "Synthesis of DI-tent-Butyl Methylenemalonate, a Sterically Hindered 1,1-Dicarbonyl Alkene," *J. Org* <http://J.Org>. Chem, (1983), vol. 48, pp. 3603-3605.

* cited by examiner

METHYLENE BETA-DIKETONE MONOMERS, METHODS FOR MAKING METHYLENE BETA-DIKETONE MONOMERS, POLYMERIZABLE COMPOSITIONS AND PRODUCTS FORMED THEREFROM

CROSS REFERENCE TO RELATED APPLICATIONS

This application is a U.S.C. §371 National Phase Application of International PCT Patent Application No. PCT/US2012/060840, filed Oct. 18, 2012, which application claims the benefit of priority to U.S. Provisional Patent Applications Ser. Nos. 61/549,104,filed Oct. 19, 2011; 61/549,092, filed Oct. 19, 2011; and 61/549,152, filed Oct. 19, 2011, the contents of each of which in their entirety are hereby incorporated herein by reference.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to a new class of methylene beta-diketone monomers, to methods of producing or synthesizing such monomers, and to the use and application of such monomers as commercial products and compositions, including, for example, monomer-based products (e.g., inks, adhesives, coatings, sealants or reactive molding) and polymer-based products (e.g., fibers, films, sheets, medical polymers, composite polymers and surfactants).

The new monomers relate to a platform of methylene beta-diketone monomers having the general structural formula:

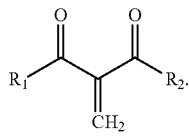

Products produced with such monomers include, for example, polymerizable compositions and polymers formed therefrom, e.g., inks, adhesives, coatings, sealants, reactive moldings, fibers, films, sheets, medical polymers, composite polymers and surfactants.

2. Background

Methylene malonate monomers have been disclosed for example in U.S. Pat. Nos. 2,313,501; 2,330,033; 3,221,745; 3,523,097; 3,557,185; 3,758,550; 3,975,422; 4,049,698; 4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and Patent Publications 2004/0076601; WO/2012/054616A2; WO2012/054633A2.

As described in certain of those publications, methylene malonates have the potential to form the basis of a large-scale platform of raw materials useful in a wide variety of chemical products.

It is envisioned that methylene beta-diketone monomers and their associated monomeric and polymeric-based products would be useful in industrial, consumer, and medical applications. Specifically, methylene beta-diketone monomers would provide a benefit over other monomers in that the incorporation of a ketone group adjacent to the active methylene group reduces the susceptibility of degradation of the monomer upon utilization or further functionalization. Indeed, unlike many other monomers, methylene beta-diketone monomers and their products can be produced via sustainable routes as well as be designed to be environmentally benign, biologically benign and as such many of the products can be generally regarded as "green."

Thus, there exists a need in the art for methods of synthesizing novel methylene beta-diketone monomers, formulating novel polymerizable compositions, and providing polymer products based on this platform.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

In one aspect, the invention provides a methylene beta-diketone monomer has a structure:

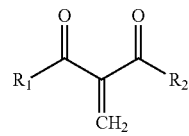

wherein $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides a method of making a methylene beta-diketone monomer comprising:

a) reacting a beta-diketone reactant having the structural formula:

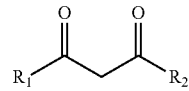

under suitable reaction conditions for sufficient time with a source of formaldehyde, optionally in the presence of an acidic or basic catalyst, and optionally in the presence of an acidic or non-acidic solvent, to form a reaction complex; and b) isolating a methylene beta-diketone monomer from the reaction complex, wherein the methylene beta-diketone monomer has the structural formula:

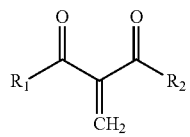

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain embodiments, the methods of the invention herein include the step of isolating the methylene beta-diketone by:
i. contacting the reaction complex, or a portion thereof, with an energy transfer means to produce a vapor phase including the methylene beta-diketone monomer; and
ii. collecting the methylene beta-diketone monomer from the vapor phase.

In other embodiments, the methods of the invention herein include isolating the methylene beta-diketone by:
i. heating the reaction complex, or a portion thereof, to a temperature between about 130° C. and about 300° C. to produce a vapor phase including the methylene beta-diketone monomer; and
ii. collecting the methylene beta-diketone monomer from the vapor phase.

In still other embodiments, the methods of the invention are performed under reaction conditions of:
a) an initiating temperature of between about 60° C. and about 130° C.;
b) atmospheric pressure.

In another aspect, the invention provides a method of preparing a methylene beta-diketone monomer comprising:
a) reacting a beta-diketone reactant having the structural formula:

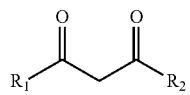

under suitable reaction conditions for sufficient time with a source of formaldehyde, optionally in the presence of an acidic or basic catalyst, and optionally in the presence of an acidic or non-acidic solvent, to form a reaction complex;

b) contacting the reaction complex, or a portion thereof, with an energy transfer means at a temperature between about 150° C. and about 300° C. to provide the reaction complex, or portion thereof, as a vapor phase; and c) isolating a methylene beta-diketone monomer from the reaction complex or portion thereof, wherein the methylene beta-diketone monomer has the structural formula:

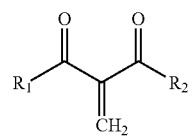

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein each instance of $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides a polymerizable composition comprising a methylene beta-diketone monomer of the invention.

In certain embodiments, the polymerizable composition is capable of bonding glass to a substrate in a time period of less than about 90 seconds, less than about 60 seconds, less than about 30 seconds, or less than about 15 seconds.

In certain other embodiments, the polymerizable composition comprising a methylene beta-diketone monomer further comprises at least one additive selected from the group consisting of an acidic stabilizer, a free radical stabilizer, a sequestering agent, a cure accelerator, a rheology modifier, a plasticizing agent, a thixotropic agents, a natural rubber, a synthetic rubbers, a filler agent and a reinforcing agent.

In another aspect, the invention provides an adhesive product comprising a methylene beta-diketone monomer of the invention.

In certain embodiments, the adhesive products have a shelf life of at least one year.

In another aspect, the invention provides a polymer formed by polymerization of one or more methylene beta-diketone monomers or a polymerizable composition thereof.

In certain embodiments, the polymers of the invention are useful as a sealant, a coating, a textile fiber, a water-treatment polymer, an ink carrier, a paint carrier, a packaging film, a molding, a medical polymer, a polymer film, a polymer fiber, or a polymer sheet.

In certain other embodiments, the polymers of the invention have repeat units of the formula:

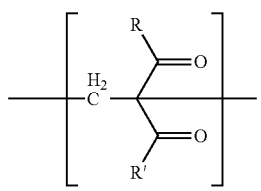

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides an oligomeric complex prepared by reacting a beta-diketone with a source of formaldehyde; optionally in the presence of heat transfer agent; optionally in the presence of an acidic or basic catalyst; and optionally in the presence of an acidic or non-acidic solvent. In certain embodiments, the oligomeric complex has between 2 and 12 repeat units having the structural formula:

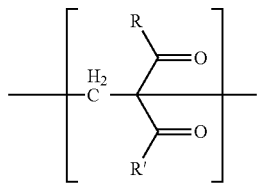

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In still another aspect, the invention provides a methylene beta-diketone monomer prepared according to the methods of the invention.

BRIEF DESCRIPTION OF THE DRAWINGS

So that those having ordinary skill in the art to which the subject invention pertains will more readily understand how to make and use the invention as described herein, preferred embodiments thereof will be described in detail below, with reference to the drawings, wherein.

DETAILED DESCRIPTION OF THE INVENTION

Overview

Figure 1:
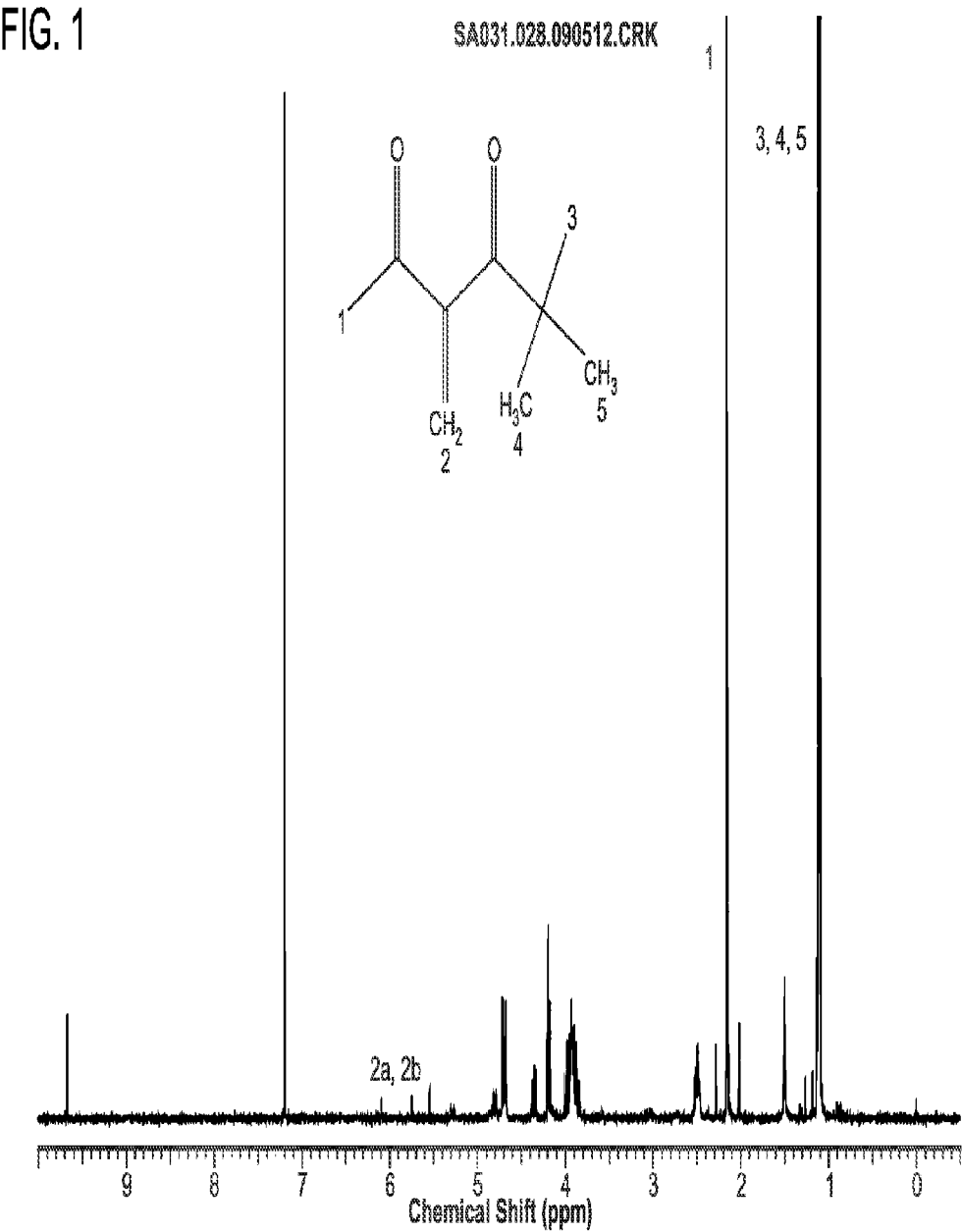
FIGS. 1 and 2 depict NMR spectra demonstrating evidence of a methylene diketone reaction product formed by the reaction of 5,5-dimethylhexane-2,4-dione and formaldehyde.

The present invention provides new and nonobvious improvements and modifications in the use and application of the Knoevenagel reaction in order to produce methylene beta-diketone monomers:

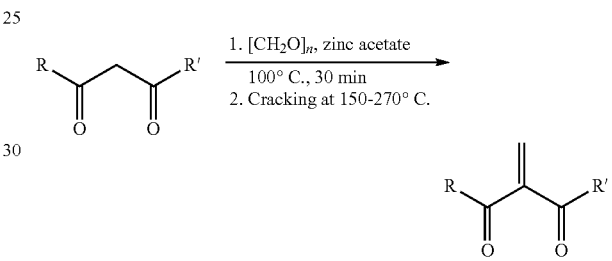

Modified Knoevenagel Reaction

While the above reaction scheme shows a direct condensation reaction, it has been discovered that an intermediary species (oligomeric complex) may be formed in certain instances. The oligomeric complex may then be cracked to yield the monomer product. As those having skill in the art will appreciate, the reaction scheme may also yield side reactions and undesired products, and unreacted starting material from which the methylene beta-diketone monomers are subsequently isolated.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "methylene beta-diketone monomer" refers to a compound having the core formula -----C(O)—C(═CH₂)—C(O)------.

As used here, the term "beta-diketone" refers to a compound having the core formula -----C(O)—CH₂—C(O)------.

As used herein, the term "reaction complex" refers to the materials which result after reacting a beta-diketone starting material with a source of formaldehyde. Such reaction complexes may comprise, without limitation, methylene beta-diketone monomers, oligomeric complexes, irreversible complex impurities, starting materials, or latent acid-forming impurities.

As used herein, the term "reaction vessel" refers to any container in which the reactants, solvents, catalysts or other materials may be combined for reaction. Such reaction vessels can be made of any material known to one of skill in the art such as metal, ceramic or glass.

As used herein, the term "vapor phase" refers to a gaseous phase which may comprise, without limitation, vaporized methylene beta-diketone monomer, vaporized starting materials; vaporized solvents, or vaporized impurities.

As used herein, the term "recovering" or "obtaining" or "isolating" refers to the removal of the monomer from the reaction mixture, vapor phase, or condensed vapor phase by one of the methods described herein, although the desired product may not be in a purified form. The term "crack" is also used to indicate depolymerization of an oligomeric complex. The desired methylene beta-diketone monomer may be obtained by "cracking" an oligomeric complex found in the reaction complex.

As used herein, the term "sterically hindered" refers to a compound in which the size of groups within the molecule prevents chemical reactions that are observed in related smaller molecules.

As used herein, the terms "volatile" and "non-volatile" refers to a compound which is capable of evaporating readily at normal temperatures and pressures, in the case of volatile; or which is not capable of evaporating readily at normal temperatures and pressures, in the case of non-volatile.

As used herein, the term "energy transfer means" refers to a means which is capable of volatizing a reaction complex, usually by, but not limited to, rapidly heating the reaction complex to temperatures from about 150° C. to about 300° C. Such energy transfer means include, but are not limited to, heat transfer agents, heat transfer surfaces, lasers, and sources of radiation.

As used herein, the term "heat transfer agent" refers to a material which is capable of achieving a high temperature and transferring that temperature to a reaction mixture. Such heat transfer agents are typically able to reach temperatures from about 150° C. to about 300° C. and include, but are note limited to silica, silicone oil, mineral oil, a petroleum based heat transfer oil or a synthetic chemical based heat transfer oil. In certain embodiments, the heat transfer agent can be pre-formed reaction complex.

As used herein the term "pre-formed reaction complex" refers to a reaction complex as defined herein which is prepared by reacting step (a) as described herein in advance of the vaporization step (b). Such pre-formed reaction complexes can be formed up to a year, up to six months, up to 3 months, up to 1 month, up to 2 weeks, up to 1 week, up to 3 days, or up to 1 day in advance of the vaporization step (b). In such instances, the vaporization step (b) is performed on a newly prepared reaction complex. In certain aspects the pre-formed reaction complex can refer to an oligomeric complex as defined herein.

As used herein the term "substantial absence" as in "substantial absence of acidic solvent" refers to a reaction mixture comprising less than 1% by weight of the particular component as compared to the total reaction mixture. In certain embodiments, a "substantial absence" refers to less than 0.7%, less than 0.5%, less than 0.4% m less than 0.3%, less than 0.2% or less than 0.1% by weight of the of the particular component as compared to the total reaction mixture. In certain other embodiments, a "substantial absence" refers to less than 1.0%, less than 0.7%, less than 0.5%, less than 0.4% m less than 0.3%, less than 0.2% or less than 0.1% by volume of the of the particular component as compared to the total reaction mixture.

As used herein, the term "stabilized," e.g., in the context of "stabilized" molecules of the invention or compositions comprising same, refers to the tendency of the molecules of the invention (or their compositions) to substantially not polymerize with time, to substantially not harden, form a gel, thicken, or otherwise increase in viscosity with time, and/or to substantially show minimal loss in cure speed (i.e., cure speed is maintained) with time.

As used herein, the term "shelf-life," e.g., as in the context of the molecules of the invention having an improved "shelf-life," refers to the molecules of the invention which are stabilized for a given period of time, e.g., 1 month, 6 months, or even 1 year or more.

Description Of Exemplary Embodiments

Methylene beta-diketone monomers in accordance with the present invention may be made by a modified Knoevenagel condensation reaction of a beta-diketone with formaldehyde under suitable reaction conditions. The general reaction scheme is provided below.

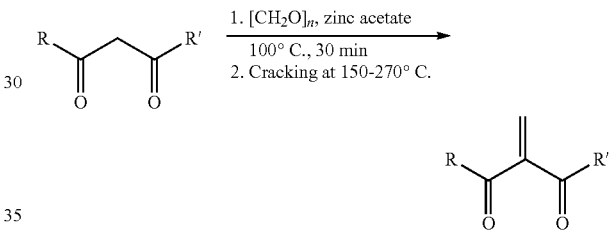

Modified Knoevenagel Reaction

Methylene Beta-Diketone Monomers

In one aspect, the invention provides a methylene beta-diketone monomer having the structural formula:

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain embodiments, the invention provides a methylene beta-diketone monomer having the structural formula:

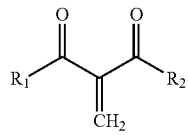

wherein each instance of $R_1$ and $R_2$ are independently $C_1$-$C_6$ alkyl, halo-($C_1$-$C_6$ alkyl), $C_3$-$C_6$ cycloalkyl, aryl, or heteroaryl, each of which may be optionally substituted by halo or $C_1$-$C_6$ alkoxy.

In still other embodiments, the invention provides a methylene beta-diketone monomer having the structural formula:

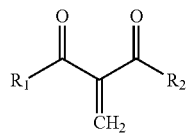

wherein each instance of $R_1$ and $R_2$ are independently $C_1$-$C_6$ alkyl or aryl.

Reactants

The reaction for making methylene beta-diketone monomers of the invention includes at least two basic reactants: a beta-diketone precursor and a source of formaldehyde.

In certain embodiments, the methylene beta-diketone precursors in accordance with exemplary embodiments disclosed herein include beta-diketones able to undergo a condensation reaction at the alpha carbon. Beta-diketone precursors include, but are not limited to, molecules having the structural formula:

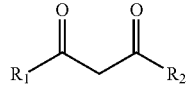

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain other embodiments, the present invention contemplates the following specifically identified beta-diketone precursors: 1,3-dimethyl-propane-1,3-diones, 1,3-diethyl-propane-1,3-diones, 1-ethyl-3-methyl-propane-1,3-diones, 1,3-dipropyl-propane-1,3-diones, 1,3-dibutyl-propane-1,3-diones, and 1,3-diphenyl-propane-1,3-diones, among others.

The beta-diketone precursor may be derived or obtained from any source, including any commercial source, derived from nature, other compounds, synthesized by other processes, etc. In certain embodiments, the beta-diketone precursors are obtained from "green" sources. For example, the beta-diketone precursors can be derived from biological sources, such as via fermentation production systems whereby microorganisms generate the beta-diketone precursors is direct metabolic by-products of fermentation—or whereby the microorganisms generate metabolic by-products of fermentation that can be then converted inexpensively to the desired beta-diketone precursors. These fermentation production systems are well-known in the art and may utilize either—or both—microorganisms derived from nature or engineered microorganisms that are specifically designed to produce the desired beta-diketone precursors products, e.g., recombinant or engineered *Escherichia coli*.

The beta-diketone precursor is reacted with a source of formaldehyde. The methods of the invention also contemplate any suitable source of formaldehyde. For example, the formaldehyde may be synthesized, derived from another chemical species (e.g., paraformaldehyde), or obtained from nature or from some other suitable source. In certain embodiments, the formaldehyde is introduced in the form of a gas. Commercial sources of formaldehyde and paraformaldehyde are readily available, which may include, for example, trioxane and formalin (e.g., aqueous formaldehyde). The source of formaldehyde may be paraformaldehyde, formalin, trioxane or gaseous formaldehyde. In certain embodiments, the formaldehyde is obtained from paraformaldehyde. In an exemplary embodiment, the source of formaldehyde is paraformaldehyde that is thermally degraded to formaldehyde in the reaction vessel. It is envisioned that other means of providing formaldehyde to the reaction vessel may be utilized, for example, a stream of gaseous formaldehyde.

Catalysts

In certain embodiments, the methods of preparing the methylene beta-diketone takes place in the presence of a suitable catalyst. However, it is envisioned that certain reactions may not required the presence of a catalyst.

In certain embodiments, the catalysts that may be used include, but are not limited to, basic catalysts such as potassium acetate, sodium acetate, zinc acetate, zinc diacetate dihydrate, aluminum acetate, calcium acetate, magnesium acetate, magnesium oxide, copper acetate, lithium acetate, aluminum oxide, or zinc oxide.

In further embodiments, the catalysts include, but are not limited to, acidic catalysts such as paratoluene sulfonic acid, dodecylbenzene sulfonic acid, boron trifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, or zinc chloride.

Still other exemplary catalysts are heterogeneous catalysts. Still other exemplary catalysts are enzyme catalysts. An exemplary enzyme is Novozym® 435 available from Novozyme. Novozym 435 is an immobilized granulate, non-specific lipase particularly useful for ester production. Neutral catalysts can also include silica and other insoluble surface-active agents.

In still further embodiments, amphoteric catalysts can include, but are not limited to, aluminum oxide, aluminum acetate, zinc acetate, magnesium acetate, and zinc oxide.

In still other embodiments, the present inventors have surprisingly and unexpectedly found that no catalyst is required to conduct the synthesis reaction of the invention. Specifically, in this embodiment, the reaction can be conducted with all of the reactants added to the reaction vessel at the start of the reaction prior to adding heat. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Solvents

The present invention contemplates that the synthesis reaction includes an acidic or non-acidic solvent, or optionally no solvent at all.

Non-acidic solvents can include, but are not limited to, tetrahydrofuran, chloroform, dichloromethane, toluene, heptane, ethyl acetate, n-butyl acetate, dibutyl ether and hexane.

Acidic solvents can include, but are not limited to acetic acid and propionic acid.

In certain embodiments, the acidic solvent is added just prior to recovery.

In certain other embodiment, optionally no solvent is needed. This zero-solvent approach will not only decrease the overall cost of production but will also help to lessen any negative impact on the environment caused by the methods of the invention, i.e., provides an environmentally-friendly approach to the synthesis of 2-methylene-1,3-disubstituted-propane-1,3-diones. An advantage of this condition is the avoidance or minimization of the formation of impurities, e.g., ketals and other latent acid-forming species.

In still other embodiments, the present inventors have surprisingly and unexpectedly found that the synthesis reaction of the invention may be conducted in the absence of both a solvent and a catalyst. Specifically, in this embodiment, the reaction can be conducted with all of the reactants added to the reaction vessel at the start of the reaction prior to adding heat and in the absence of a solvent. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Stabilization

Certain embodiments of the present invention provide monomers that are amenable to anionic polymerization. Therefore, to prevent unwanted polymerization and extend shelf life, certain exemplary embodiments include suitable acidic stabilizers, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Reaction Conditions

In certain embodiments of the present invention, the starting precursor is reacted with paraformaldehyde in the presence of a catalyst (e.g., zinc acetate dehydrate) at 60° C.-130° C. (e.g., 100° C.) for at least about 30 minutes. The resulting intermediate material (e.g., oligomeric complex) is then thermally depolymerized to the vinyl containing product by addition to a hot surface set from 150° C. to 270° C. The resulting crude monomer is then purified, for example by distillation, fractional distillation or other separation methods.

For a typical lab scale reaction: a 3-neck 250 mL round bottom reaction flask was equipped with an overhead stirrer, a heating mantle, and a temperature probe connected to a temperature controller. The reaction flask was adequately vented to the back of the hood to reduce the possibility of pressure build-up. The beta-diketone (precursor), paraformaldehyde (1.8 equiv) and zinc acetate (0.001 equiv) were added to the reaction flask. The contents of the flask were mixed for approximately 2 minutes prior to the application of heat. After the initial mixing period the temperature controller was set to 100° C. The heterogeneous reaction mixture was allowed to heat with the temperature for dissolution and onset of exotherm being noted. Once a rapid increase in temperature was observed, heating was discontinued. Once the exotherm subsided, the heating mantle was immediately removed and the reaction mixture (herein "reaction complex") was allowed to cool to room temperature to afford the oligomeric mixture.

To isolate the methylene beta-diketone monomer from the reaction complex, a 4-neck suitable round bottom flask was equipped with a mechanical stirrer, heating mantle, a thermocouple connected to a temperature controller, an addition funnel, a Claisen adapter, and a vacuum adapter connected to a receiver one-neck round bottom flask which was placed in an ice-bath. The system was evacuated to low pressure (1-250 mmHg). The oligomeric mixture was added to the addition funnel. The reaction flask was then applied via the connected heating mantle to 150-270° C. Once the temperature inside the flask reached the desired range, a drop-wise addition of the oligomer (reaction complex) to reaction flask was started. The addition rate was maintained so that the set temperature was maintained in the desired range. After the addition was complete, the heating mantle was turned off and the system was allowed to cool to room temperature, at this point the system was opened to atmospheric pressure. An aliquot was then taken for analysis and the remaining cracked distillate was either distilled further via fractional distillation to improve purity or placed in a refrigerator.

This general reaction scheme was utilized to provide the examples provided herein. Due to the wide variety of example obtained, it is envisioned that this general reaction scheme can be utilized to provide a wide array of methylene beta-diketone monomers as set forth herein. Further, it is envisioned that modifications can be made to this general reaction scheme in order to improve efficiencies and purity of the product obtained.

Methods of Synthesis

In another aspect, the invention provides a method of preparing methylene beta-diketone monomers according to the reaction scheme disclosed herein.

In certain embodiments, the method for preparing the methylene beta-diketone monomers comprises:
a) reacting a beta-diketone reactant having the structural formula:

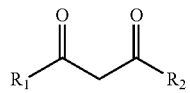

under suitable reaction conditions for sufficient time with a source of formaldehyde, optionally in the presence of an acidic or basic catalyst, and optionally in the presence of an acidic or non-acidic solvent, to form a reaction complex; and
b) isolating a methylene beta-diketone monomer from the reaction complex, wherein the methylene beta-diketone monomer has the structural formula:

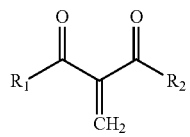

wherein $R_1$ and $R_2$ are defined above.

In certain embodiments, the reaction may be initiated at temperatures between about 60° C. to about 130° C., at atmospheric pressure. It is contemplated that the reaction conditions may be modified depending on the source of formaldehyde. For example, when paraformaldehyde is utilized within the reaction vessel, the initial temperature must be high enough to make free formaldehyde available for the reaction. If another source of formaldehyde is utilized, those having skill in the art will appreciate that the reaction conditions may be modified accordingly. Exemplary sources include paraformaldehyde, formalin, trioxane, gaseous formaldehyde, or any reaction or process in which formaldehyde is liberated.

In other embodiments, the methylene beta-diketone monomer may be isolated from the reaction complex by contacting the reaction complex, or a portion thereof, with an energy transfer means to produce a vapor phase including the methylene beta-diketone monomer; and collecting the methylene beta-diketone monomer from the vapor phase.

In still other embodiments, the methylene beta-diketone monomer may be isolated from the reaction complex immediately, or the reaction complex may be stored, preferably refrigerated, until a later time. In an exemplary embodiment, the reaction complex is not acid stabilized prior to isolating the methylene beta-diketone monomer.

In other embodiments, the reaction complex, or a portion thereof, may be heated to a vapor phase and condensed in order to isolate the methylene beta-diketone monomer. The reaction complex may be heated to a temperature between about 130° C. and about 300° C.

In still other embodiments, the reaction complex, or a portion thereof, may come in contact with an energy transfer means in order to facilitate isolation of the monomer. In an exemplary embodiment, the reaction complex, or portion thereof, may be vaporized in a very short time, for example less than 15 minutes, preferably less than 1 minute, more preferably less than 30 seconds, and less than 1 second. Certain exemplary embodiments contemplate vaporizing the reaction complex in a continuous manner as it is formed during the reaction step.

Exemplary energy transfer means include a heat transfer agent, a heat exchanger, a laser, microwave energy, sonic energy, electromagnetic energy, and a source of radiation, or any combination thereof. The energy transfer means operates to quickly vaporize the reaction complex (or portion thereof) to permit isolation of the monomer product. For example, an oligomeric complex may be formed, and the energy transfer means is utilized to "crack" or depolymerize the oligomer to allow isolation of the monomer. In certain embodiments, the oligomeric complex may include oligomers of 2-12 units able to provide monomer product upon crack.

In certain exemplary embodiments, the heat transfer agent is a heated inert gas, one or more metal beads, one or more glass beads, one or more porcelain beads, sand, silica, silicone oil, mineral oil, a petroleum based heat transfer oil, a synthetic chemical based heat transfer oil, or a pre-formed portion of the reaction complex.

In certain other embodiments, the heat exchanger is a shell and tube heat exchanger, a plate heat exchanger, and adiabatic wheel heat exchanger, a finned pipe heat exchanger, a plate fin heat exchanger, or a scraped surface heat exchanger.

In still other embodiments, the vapor phase of the reaction complex is condensed, and the condensate is subject to one or more further separation processes. For example, the separation process may include any of simple distillation, fractional distillation, flash distillation, steam distillation, vacuum distillation, short path distillation, thin-film distillation, reactive distillation, pervaporation, extractive distillation, flash evaporation, rotary evaporation, liquid/liquid extraction, centrifuging, or any combination thereof, and other techniques known to those having skill in the art.

Compositions

The methylene beta-diketone monomers of the invention can be incorporated into any number of compositions and products including but not limited to reactive monomer-based compositions, reactive oligomer-based compositions and reactive polymer-based compositions.

Exemplary compositions can be analyzed by placing a drop of a monomer composition on a substrate (for example a glass slide or 4"×1" polycarbonate sample). Another glass slide or piece of polycarbonate is pressed on top over the monomer-covered area. The time is then immediately recorded from pressing the top-slide till the two slides are bonded tightly. In such embodiments, the exemplary composition is capable of bonding glass to a substrate in less than about 90 seconds, less than about 60 seconds, less than about 30 seconds or less than about 15 seconds. Similarly, the exemplary composition is capable of bonding polycarbonate to a substrate in less than about 90 seconds, less than about 60 seconds, less than about 45 seconds or less than about 30 seconds.

Alternatively, exemplary compositions can be analyzed by mixing 0.5 ml of monomer with 0.3 ml of 3% tertiary butyl ammonium fluoride (TBAF) in Dibutyl Phthalate solution. The time is recorded from adding the TBAF solution till the mixture become solid with vigorous stirring or mixing. In such embodiments, said composition solidifies upon addition of 3% tertiary butyl ammonium fluoride (TBAF) in Dibutyl Phthalate solution in less than about 15 seconds, less than about 10 seconds, or less than about 7 seconds.

Alternatively still, the exemplary compositions can be analyzed by placing 0.5 ml of monomer into a test tube and cap with a cork stopper and keeping the test tubes containing monomers at 25° C., or in ovens at 55° C. or 82° C. In each case the storage stability test is performed at atmospheric pressure. Time is recorded when the monomer became a gel or solid. In such embodiments, said composition remains stable at 25° C. and at atmospheric pressure for more than 10 days, more than 15 days, more than 20 days, more than 25 days or more than 30 days. Similarly, said composition remains stable at 82° C. and at atmospheric pressure for more than about 2 hours, more than about 3 hours, or more than about 4 hours.

Exemplary compositions include, but are not limited to an adhesive, a coating, a sealant, a composite, or a surfactant.

Additionally polymer products include, but are not limited to, a sealant, a thermal barrier coating, a textile fiber, a water-treatment polymer, an ink carrier, a paint carrier, a packaging film, a molding, a medical polymer, a polymer film, a polymer fiber or a polymer sheet.

In each case, the exemplary compositions may be formulated to include one or more materials to extend the shelf-life as well as control the onset of cure of the materials. In certain embodiments, the compositions are formulated such that the composition is stable for at least 1 month, or for at least 2 months, or for at least 3 months, or for at least 4 months, or for at least 5 months, or for at least 5-10 months, or for at least 10-20 months, or for at least 20-30 months. Preferably, the adhesive composition comprising the methylene beta-diketone monomers or other commercial compositions or products, are stable for at least one year.

Such formulation materials include acidic stabilizer, volatile acid stabilizers, acidic gases, free radical stabilizers, sequestering agents, cure accelerators and rheology modifiers.

Exemplary embodiments contemplate any suitable acidic stabilizer known in the art, including, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Volatile acid stabilizers include any material which can be added to the monomer or polymer compositions to extend shelf-life and stabilize the vapor phase above the composition upon storage, e.g., acidic gases. Such volatile acid stabilizers may have a boiling point, for example, less than about 200° C.; less than about 170° C.; or less than about 130° C.

Acidic gases include any gaseous material which can be added to the monomer or polymer compositions to extend shelf-life and stabilize the vapor phase above the composition upon storage. Such acid gases can include, but are not limited to, $SO_2$ or $BF_3$.

For each of these acidic stabilizing materials, such acidic stabilizer can be present in a concentration of about 0.1 ppm to about 100 ppm; about 0.1 ppm to about 25 ppm; or about 0.1 ppm to about 15 ppm.

Free radical stabilizers can include any material capable of stabilizing or inhibiting free radical polymerization of the material upon standing. In one embodiment, the free radical stabilizers are phenolic free radical stabilizers such as, HQ (hydroquinone), MEHQ (methyl-hydroquinone), BHT (butylated hydroxtoluene) and BHA (butylated hydroxyanisole). In certain embodiments, the free radical stabilizers are present in a concentration of 0.1 ppm to 10,000 ppm; 0.1 ppm to 3000 ppm; or 0.1 ppm to 1500 ppm. In certain other embodiments, particularly where a free radical or ultraviolet cure will be utilized, the free radical stabilizers are present in a concentration of 0.1 ppm to 1000 ppm; 0.1 ppm to 300 ppm; or 0.1 ppm to 150 ppm.

Sequestering agents include any material capable of enhancing the bonding of materials containing acid salts such as paper or wood. Such sequestering agents include, but are not limited to crown ethers, silyl crowns, calixarenes and polyethylene glycols. Sequestering agents also enhance the utility of surface accelerators that are acid salts applied to surfaces to control the rate of cure of the materials.

Cure accelerators include any material capable of speeding the rate of cure of the methylene beta-diketone monomers. Cure accelerators also include any material capable of speeding the cure through volume of the applied composition. Such cure accelerators include but are not limited to sodium or potassium acetate; acrylic, maleic or other acid salts of sodium, potassium lithium copper and cobalt; salts such as tetrabutyl ammonium fluoride, chloride, or hydroxide; or chemically basic materials such as amines and amides, or salts of polymer bond acids, benzoate salts, 2,4-pentanedionate salts, sorbate salts, or propionate salts. Such cure accelerators can be added directly to the exemplary compositions or applied to the material to be bonded prior to addition of the composition.

Rheology modifiers include any material which can modify the viscosity of the exemplary compositions as well as thixotropic properties for greater utility in certain applications. Rheology modifiers include, but are not limited to, hydroxyethylcellulose, ethyl hydroxyethylcellulose, methylcellulose, polymeric thickeners, pyrogenic silica or a combination thereof.

In certain embodiments, the exemplary compositions may include tougheners. Such tougheners include, but are not limited to, acrylic rubbers; polyester urethanes; ethylene-vinyl acetates; fluorinated rubbers; isoprene-acrylonitrile polymers; chlorosulfonated polyethylenes; homopolymers of polyvinyl acetate; and reaction products of the combination of ethylene, methyl acrylate and monomers having carboxylic acid cure sites, which once formed are then substantially free of processing aids and anti-oxidants; and combinations thereof. In certain embodiments, the tougheners include those disclosed in U.S. Pat. No. 4,440,910 (O'Connor), directed to rubber toughened cyanoacrylate compositions through the use of certain organic polymers as toughening additives that are elastomeric, i.e., rubbery, in nature, such as acrylic rubbers; polyester urethanes; ethylene-vinyl acetates; fluorinated rubbers; isoprene-acrylonitrile polymers; chlorosulfonated polyethylenes; and homopolymers of polyvinyl acetate. In certain embodiments, the toughener is an elastomeric polymer which is a copolymer of methyl acrylate and ethylene, manufactured by DuPont, under the name of VAMAC, such as VAMAC N123 and VAMAC B-124. VAMAC N123 and VAMAC B-124 are reported by DuPont to be a master batch of ethylene/acrylic elastomer. In other embodiments, the toughener may be the DuPont materials called VAMAC B-124, N123, VAMAC G, VAMAC VMX 1012 or VCD 6200. In other instances, the toughener may be a rubber toughening component having (a) reaction products of the combination of ethylene, methyl acrylate and monomers having carboxylic acid cure sites, (b) dipolymers of ethylene and methyl acrylate, and combinations of (a) and (b), which once the reaction products and/or dipolymers are formed are then substantially free of processing aids, such as the release agents octadecyl amine (reported by DuPont to be available commercially from Akzo Nobel under the tradename ARMEEN 18D), complex organic phosphate esters (reported by DuPont to be available commercially from R.T. Vanderbilt Co., Inc. under the tradename VANFRE VAM), stearic acid and/or polyethylene glycol ether wax, and anti-oxidants, such as substituted diphenyl amine (reported by DuPont to be available commercially from Uniroyal Chemical under the tradename NAUGARD 445). Commercial examples of such rubber tougheners include VAMAC VMX 1012 and VCD 6200 rubbers, and these may be used too.

The exemplary compositions containing methylene beta-diketone monomer may also optionally include other additives, such as plasticizing agents, thixotropic agents, natural or synthetic rubbers, filler agents, and reinforcing agents, etc. Such additives are well known to those skilled in the art.

The exemplary compositions containing methylene beta-diketone monomer may optionally include at least one plasticizing agent that imparts flexibility to the polymer formed from the methylene beta-diketone monomer. The plasticizing agent preferably contains little or no moisture and should not significantly affect the stability or polymerization of the monomer. Such plasticizers are useful in polymerized compositions to be used in any application in which flexibility of the adhesive or polymer product is desirable.

Examples of suitable plasticizers include, without limitation, acetyl tributyl citrate, dimethyl sebacate, triethyl phosphate, tri (2-ethylhexyl)phosphate, tri (p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts less than about 60 weight %, or less than about 50 weight %, or less than about 30 weight %, or less than about 10 weight %, or less than about 5 weight %, or less than about 1 weight % or less, provides increased film strength (e.g., toughness) of the polymerized monomer over polymerized monomers not having plasticizing agents.

The exemplary compositions containing methylene beta-diketone monomer may also optionally include at least one thixotropic agent, i.e., the property of exhibiting a high fluidity during deformation by force of a sprayer, roller or trowel, but losing the fluidity when left at rest. Suitable thixotropic agents are known to the skilled artisan and include, but are not limited to, silica gels such as those treated with a silyl isocyanate. Examples of suitable thixotropic agents are disclosed in, for example, U.S. Pat. Nos.: 4,720,513 or 4,510,273, the disclosures of which are hereby incorporated in their entireties.

The exemplary compositions containing methylene beta-diketone monomer may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The exemplary compositions containing methylene beta-diketone monomer may also optionally comprise one or more other reinforcing agents (e.g., fibrous reinforcements) other than natural or synthetic rubber to impart impact resistance and/or to impart structural strength or to provide shape or form. Examples of such agents are well known in the art. Examples of suitable fibrous reinforcement include PGA microfibrils, collagen microfibrils, cellulosic microfibrils, and olefinic microfibrils. The compositions may also contain colorants such as dyes, pigments, and pigment dyes. Examples of suitable colorants include 6-hydroxy-5-[(4-sulfophenyl)axo]-2-naphthalene-sulfonic acid (FD+ C Yellow No. 6); 9-(o-carboxyphenyl)-6-hydroxy-2,4,5,7-tetraiodo-3H-xanthen-3-one monohydrate (FD+C Red No. 3); and 2-(1,3-dihydro-3-oxo-5-sulfo-2H-indol-2-ylidene)-2,3-dihydro-3-oxo-1H-indole-5-sulfonic acid (FD+ C Blue No. 2), wherein the suitable colorant should not destabilize the monomer.

The exemplary compositions containing methylene beta-diketone monomer may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions containing methylene beta-diketone monomer, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents.

Other compositions and additives contemplated herein, include additional stabilizers, accelerators, plasticizers, fillers, opacifiers, inhibitors, thixotrophy conferring agents, dyes, fluorescence markers, thermal degradation reducers, adhesion promoters, thermal resistance conferring agents and combinations thereof, and the like, some of which are exemplified by U.S. Pat. Nos. 5,624,669; 5,582,834; 5,575,997; 5,514,371; 5,514,372; 5,312,864 and 5,259,835, the disclosures of all of which are hereby incorporated in their entirety by reference.

Depending on whether the composition is a monomer-based composition (e.g., inks, adhesives, coatings, sealants or reactive molding) or a polymer-based composition (e.g., fibers, films, sheets, medical polymers, composite polymers and surfactants), one having ordinary skill in the art will have the knowledge and skill by which to formulate such compositions and/or products without undue experimentation having suitable amounts, levels and combinations of the above types of additives and components.

Additionally, polymerizable compositions may be formulated to include additives such as acidic stabilizers, a free radical stabilizers, a sequestering agents, a cure accelerators, rheology modifiers, a plasticizing agents, a thixotropic agents, natural rubbers, synthetic rubbers, filler agents, reinforcing agents and the like. Such additives are provided at levels sufficient to achieve the desired results which can readily be determined by those having skill in the art.

For certain exemplary embodiments, an acidic stabilizer is present in a concentration of about 0.1 ppm to about 100 ppm, about 0.1 ppm to about 25 ppm, or about 0.1 ppm to about 15 ppm, by weight of the composition.

For certain exemplary embodiments, a free radical stabilizer is present in a concentration selected from about 0.1 ppm to about 10000 ppm, about 0.1 ppm to about 3000 ppm, about 0.1 ppm to 1500 ppm, about 0.1 ppm to about 1000 ppm, about 0.1 ppm to about 300 ppm, or about 0.1 ppm to about 150 ppm, by weight of the composition.

For certain exemplary embodiments, a sequestering agent, such as a crown ether, a silyl crown, a calixarene, a polyethylene glycol, or a combination thereof may be utilized.

For certain exemplary embodiments, a cure accelerator, such as sodium acetate, potassium acetate, tetrabutyl ammonium fluoride, tetrabutyl ammonium chloride, tetrabutyl ammonium hydroxide, a benzoate salt, a 2,4-pentanedionate salt, a sorbate salt, and a propionate salt, may be utilized.

For certain exemplary embodiments, a rheology modifier, such as hydroxyethylcellulose, ethyl hydroxyethylcellulose, methylcellulose, a polymeric thickener, and pyrogenic silica, may be utilized.

Exemplary polymerizable compositions are stable at 25° C. and at atmospheric pressure for more than 10 days, more than 15 days, more than 20 days, more than 25 days, or more than 30 days. Certain exemplary embodiments may exhibit a shelf life of up to one year, or up to two years. Certain exemplary embodiments may be tested for stability at elevated temperature, e.g., 82° C., at atmospheric pressure. Certain exemplary embodiments may exhibit elevated temperature stability for more than 2 hours.

Certain exemplary embodiments disclosed herein relate to polymers and polymer products formed by polymerization of the polymerizable compositions comprising the methylene beta-diketone monomers.

Polymers and polymer products envisioned include coatings, paints, fibers, composites, textile fibers, water-treatment polymers, ink carriers, paint carriers, packaging films, moldings, medical polymers, polymer films, polymer fibers, polymer sheets, and the like. As discussed earlier, the methylene beta-diketone monomers are capable of supporting a vast array of products due to the activity of the methylene group and the ability to vary the functional groups R, R' as shown in the structure of the repeating unit:

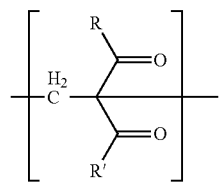

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

Oligomeric Complex Products

The reaction of the precursor beta-diketone with the source of formaldehyde may result in an oligomeric complex which is subsequently cracked to obtain the desired methylene beta-diketone monomer. Certain oligomeric complexes are capable of being efficiently vaporized or "cracked" into high purity monomers of 2-methylene-1,3-disubstituted-propane-1,3-dione by rapid vaporization as described herein.

As such, the invention provides an oligomeric complex prepared by reacting a 1,3-disubstituted-propane-1,3-dione with a source of formaldehyde; optionally in the presence of heat transfer agent; optionally in the presence of an acidic or basic catalyst; and optionally in the presence of an acidic or non-acidic solvent. In certain embodiments, the oligomeric complex comprises between 2 and 12 repeat units that are able to yield monomer upon cracking The invention further provides an oligomeric complex prepared by reacting a 1,3-disubstituted-propane-1,3-dione with a source of formaldehyde in a substantial absence of acidic solvent; optionally in the presence of heat transfer agent; optionally in the presence of an acidic or basic catalyst; and optionally in the presence of a non-acidic solvent. In certain embodiments, the substantial absence of acidic solvent represents less than 1.0%, less than 0.5%, less than 0.2% or less than 0.1% by weight acidic solvent as compared to the total composition of the reaction mixture.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Analytical Methods

The structures of monomers of this invention were confirmed using one or more of the following procedures.

NMR

Samples were diluted in deuterated chloroform prior to $^1$H NMR spectroscopy at 300 MHz (Bruker). A more concentrated sample was also prepared in a solution of 0.01 M Cr(III) acetoacetonate in deuterated chloroform and was analyzed by quantitative $^{13}$C NMR spectroscopy at 75 MHz. Samples were not purified.

Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

atm atmosphere
br s broad singlet
C Celsius
d doublet
dd doublet of doublets
MM substituted 3-methylene-2,4-pentanebeta-ketoester
HQ hydroquinone
GC-MS Gas Chromatography-Mass Spectroscopy
g gram
h hour, hours
$^1$H NMR proton nuclear magnetic resonance
J coupling constant (NMR spectroscopy)

L liter
M mol·L$^{-1}$ (molar)
m multiplet
MHz megahertz
min minute, minutes
mL milliliter
mM millimolar
mol mole
MS mass spectrum, mass spectroscopy
m/z mass-to-charge ratio
N equivalents·L$^{-1}$ (normal)
NMR Nuclear Magentic Resonance
pH negative logarithm of hydrogen ion concentration
q quartet
rt room temperature
singlet
t triplet
RB, RBF round bottom flask The following concrete examples were made in accordance with the general reaction scheme set forth above, unless otherwise noted.

Example 1

Reaction of 5,5-dimethylhexane-2,4-dione and formaldehyde

The reaction scheme disclosed herein was performed using 5,5-dimethylhexane-2,4-dione and formaldehyde (obtained from paraformaldehyde). The following monomer was obtained.

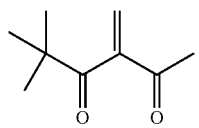

Figure 2:
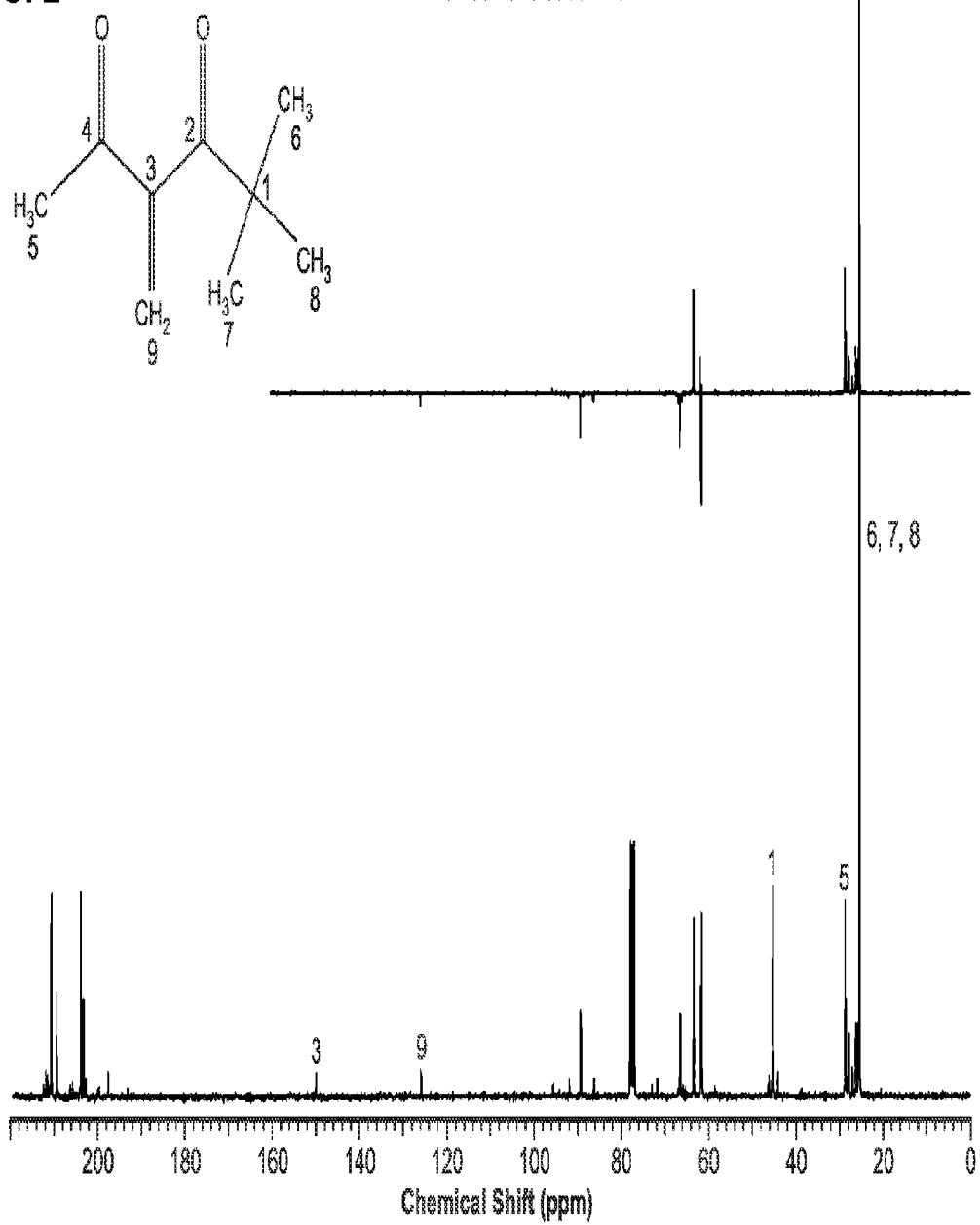

The two small peaks at 5.75 and 6.2 ppm in the 1H spectrum (FIG. 1) and the peaks at 126 (CH2) and 150 ppm (quaternary) in the 13C spectrum (FIG. 2) are consistent with the geminal CH2 functionality of the desired structure (below). The DEPT-135 spectrum (FIG. 2) is also shown.

Example 2

Reaction of heptane-3,5-dione and formaldehyde

The reaction scheme disclosed herein was performed using heptane-3,5-dione and formaldehyde (obtained from paraformaldehyde). The following monomer was obtained.

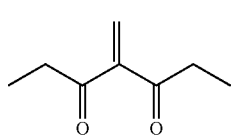

Figure 3:
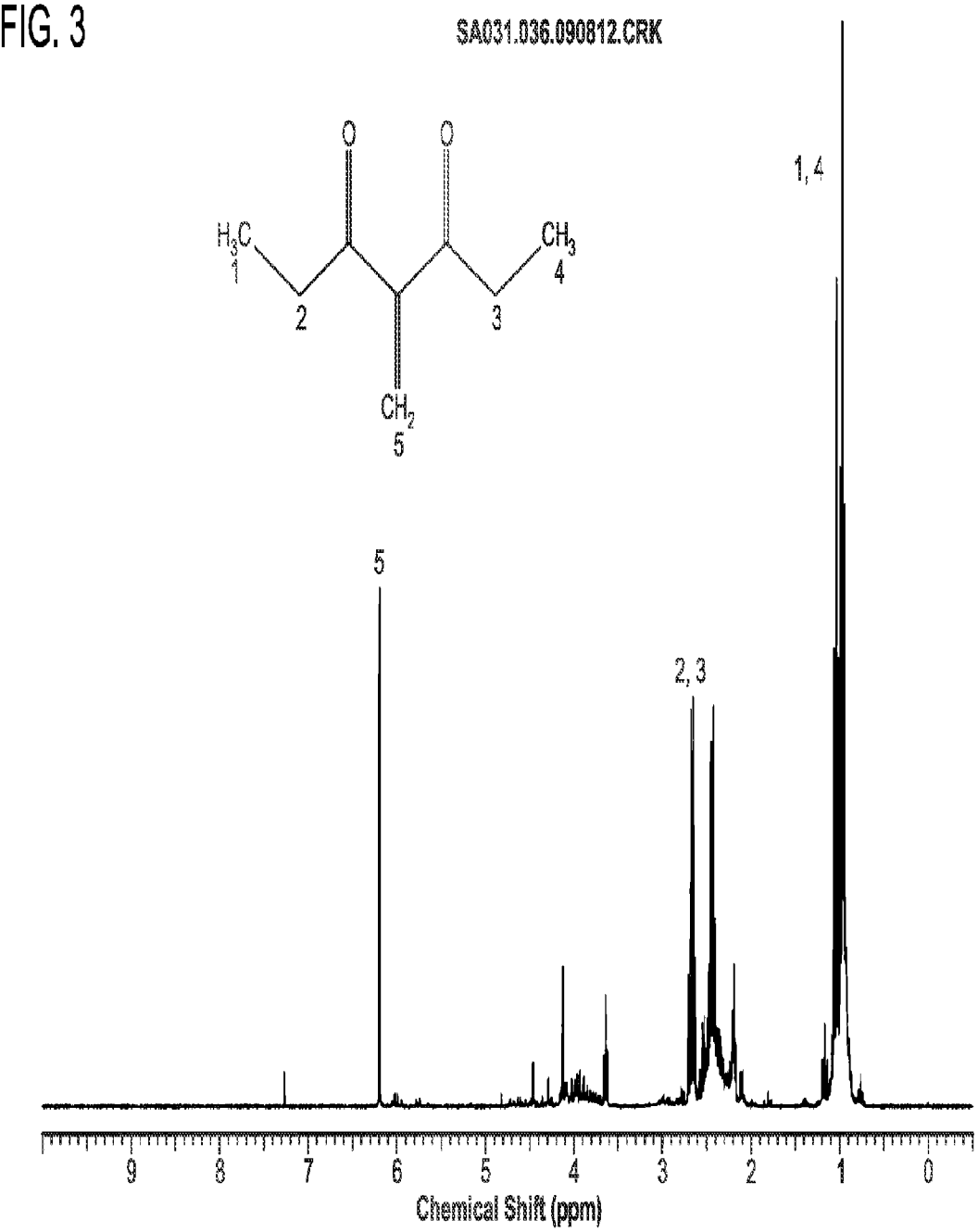
FIG. 3 depicts an NMR spectrum demonstrating evidence of a methylene diketone reaction product formed by the reaction of heptane-3,5-dione with formaldehyde.

The peak at 6.2 ppm in the $^1$H NMR spectrum (FIG. 3) is consistent with the geminal CH$_2$ peak of the product:

Example 3

Reaction of 5-methylhexane-2,4-dione and formaldehyde

The reaction scheme disclosed herein was performed using 5-methylhexane-2,4-dione and formaldehyde (obtained from paraformaldehyde). The following monomer was obtained.

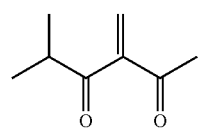

Figure 4:
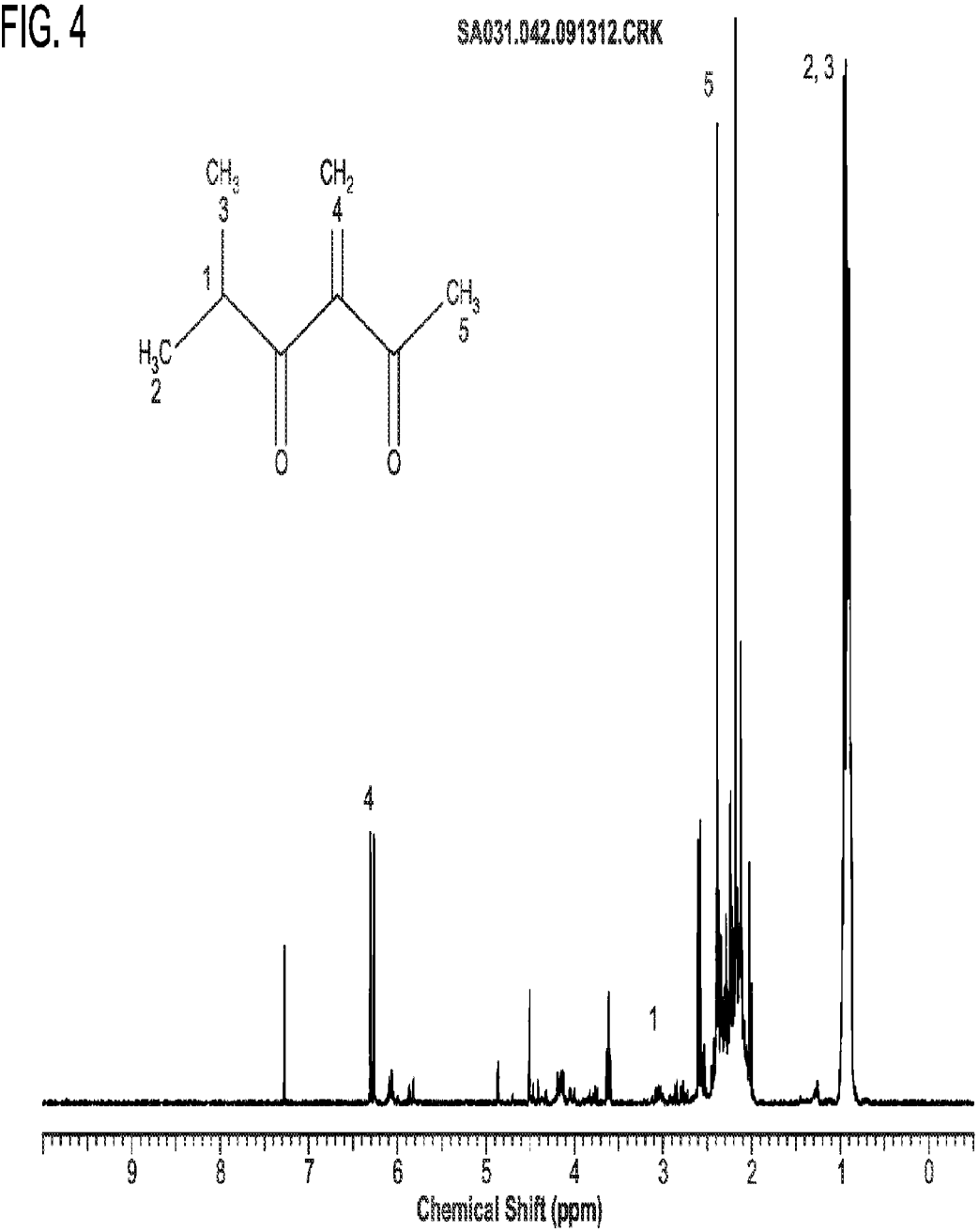
FIG. 4 depicts an NMR spectrum demonstrating evidence of a methylene beta-diketone reaction product formed by the reaction of 5-methylhexane-2,4-dione with formaldehyde.

The peaks at 6.2 and 6.3 ppm in the $^1$H NMR spectrum in FIG. 4 are consistent with the geminal CH$_2$ peak of the product.

Example 4

Reaction of 1-phenylbutane-1,3-dione and formaldehyde

The reaction scheme disclosed herein was performed using 1-phenylbutane-1,3-dione and formaldehyde (obtained from paraformaldehyde). The following monomer was obtained.

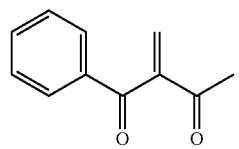

Figure 5:
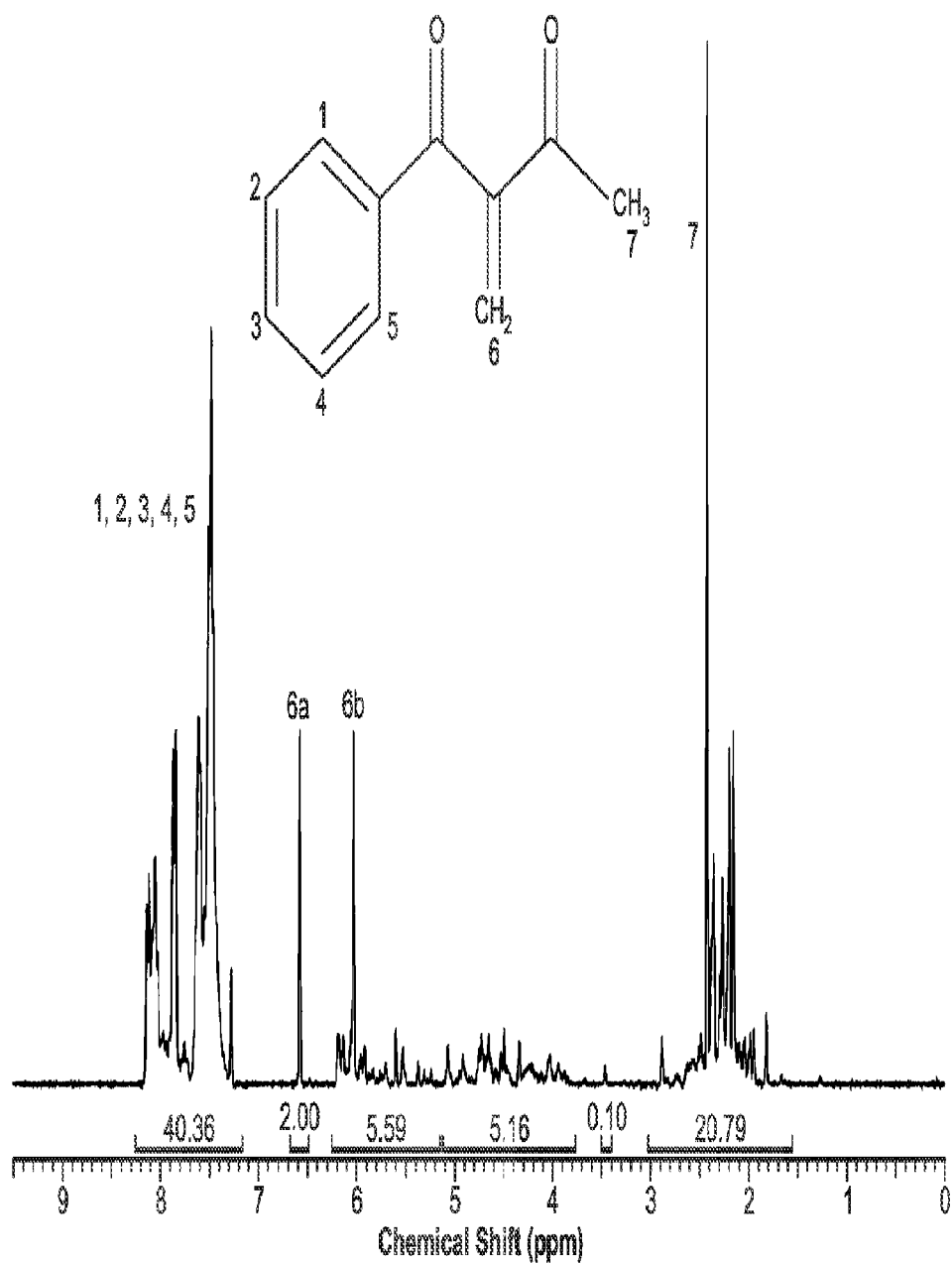
FIGS. 5 and 6 depict NMR spectra demonstrating evidence of a methylene diketone reaction product formed by the reaction of 1-phenylbutane-1,3-dione with formaldehyde.
Figure 6:
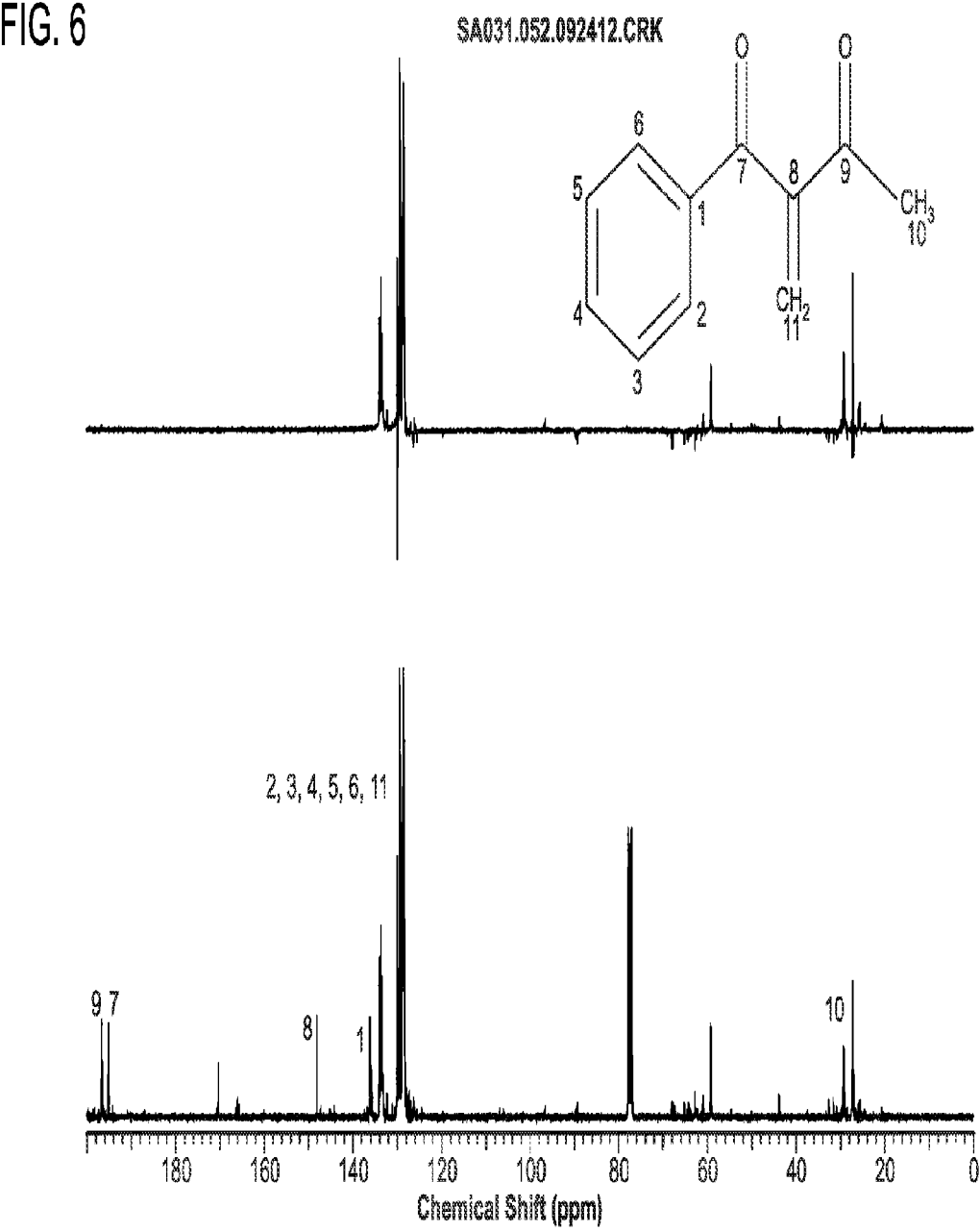
Figure 7:
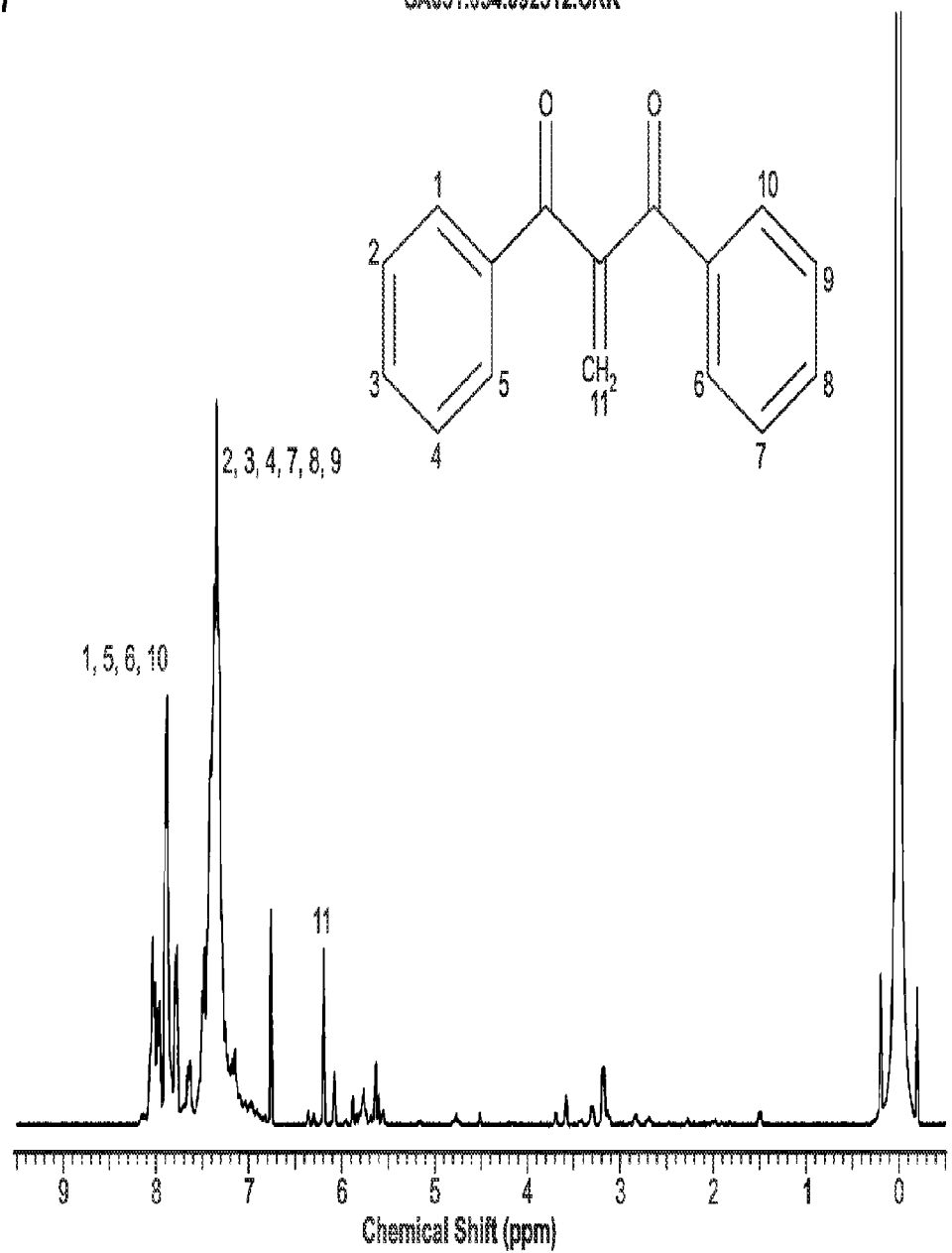
FIG. 7 depicts an NMR spectrum demonstrating evidence of a methylene diketone reaction product formed by the reaction of 1,3-diphenylpropane-1,3-dione with formaldehyde.

The peaks at 6.1 and 6.6 ppm in the $^1$H NMR spectrum of FIG. 5 are consistent with the geminal CH$_2$ peak of the product. The peaks at 130 ppm (CH2) and 148 ppm (quaternary) in the $^{13}$C and DEPT-135 NMR spectra in FIG. 6 are also consistent with the product.

Example 5

Reaction of 1,3-diphenylpropane-1,3-dione and formaldehyde

The reaction scheme disclosed herein was performed using 1,3-diphenylpropane-1,3-dione and formaldehyde (obtained from paraformaldehyde). The following monomer was obtained.

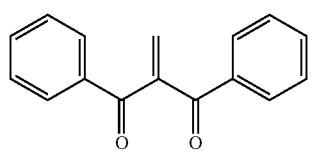 [SMILES: C=C(C(=O)c1ccccc1)C(=O)c1ccccc1]

Example 6

Reaction of nonane-4,6-dione and formaldehyde

Potassium tert-butoxide (97.5 g, 0.87 mol) was added to a 1 L 3-neck flask containing 150 mL dry dimethyl formamide and equipped with a mechanical stirrer and a thermocouple. The temperature was raised to 50° C. with stirring. Methyl butyrate (200 mL, 1.8 mol) and 2-pentanone (62 mL, 0.58 mol) were added as a mixture via 500 mL addition funnel over 2.5 h at 50° C. during which the yellow slurry turned to a clear brown solution. The reaction mixture was stirred for an additional 5 h at 50° C. at which point heating was turned off and the reaction mixture was allowed to stir for 14 h at room temperature. The reaction mixture was quenched by slow addition into a 1 M HCl aq. solution (500 mL) at 0° C., and the pH was adjusted with 1 M HCl aq. solution to about 5. The reaction slurry was extracted with heptane (4×400 mL). The combined organic layers were concentrated to 300 mL under reduced pressure. The residue was washed with water (5×400 mL) followed by a brine wash. The enriched organic layer was further concentrated under reduced pressure to afford a yellowish liquid which was purified by distillation at 65° C., 2 Torr to afford 60 g of 85% pure (based on H NMR analysis) material (56% yield) as a clear liquid.

The following monomer was obtained.

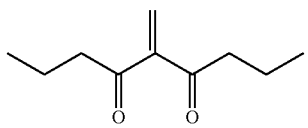

Figure 8:
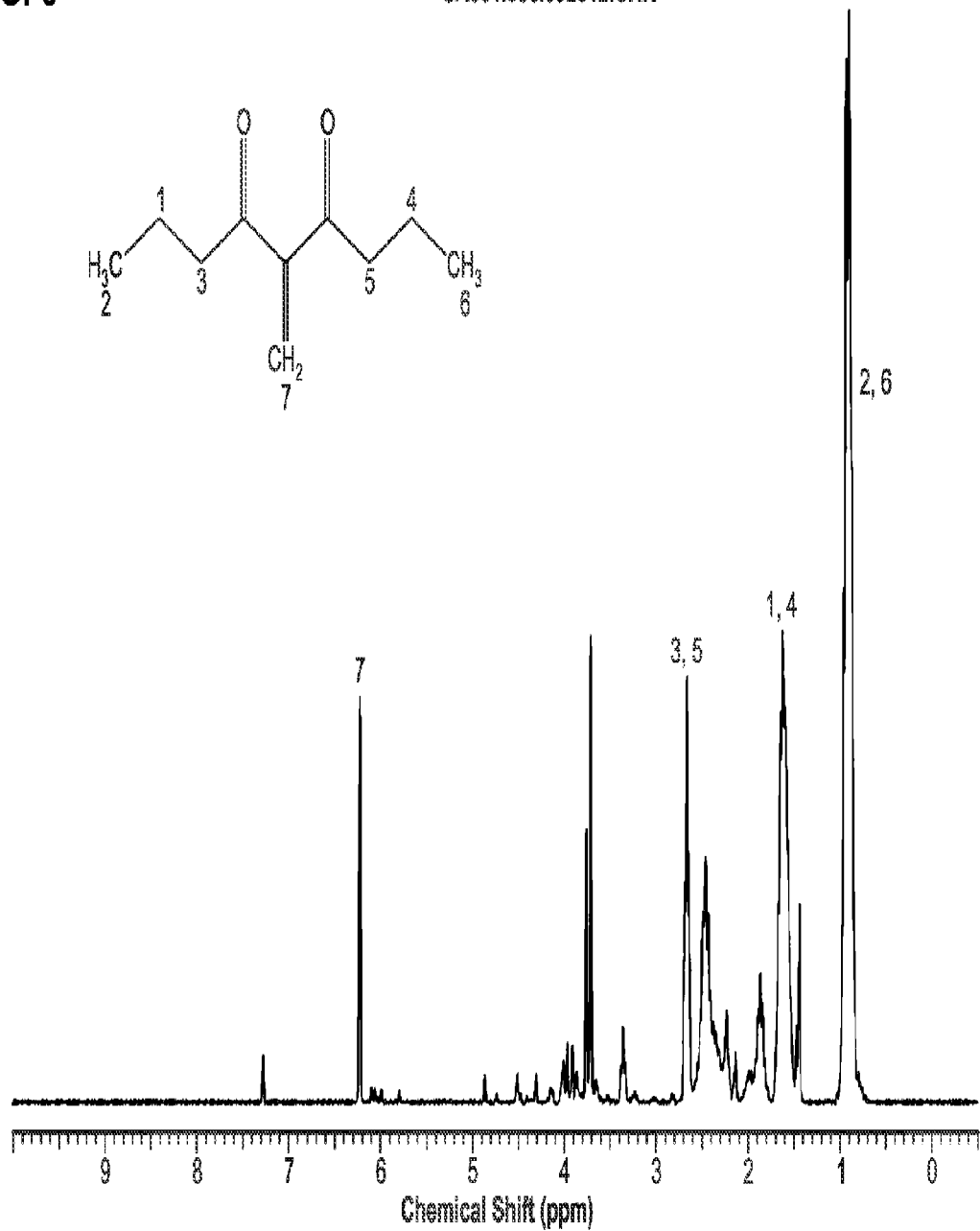
FIGS. 8 and 9 depict NMR spectra demonstrating evidence of a methylene diketone reaction product formed by the reaction of nonane-4,6-dione with formaldehyde.
Figure 9:
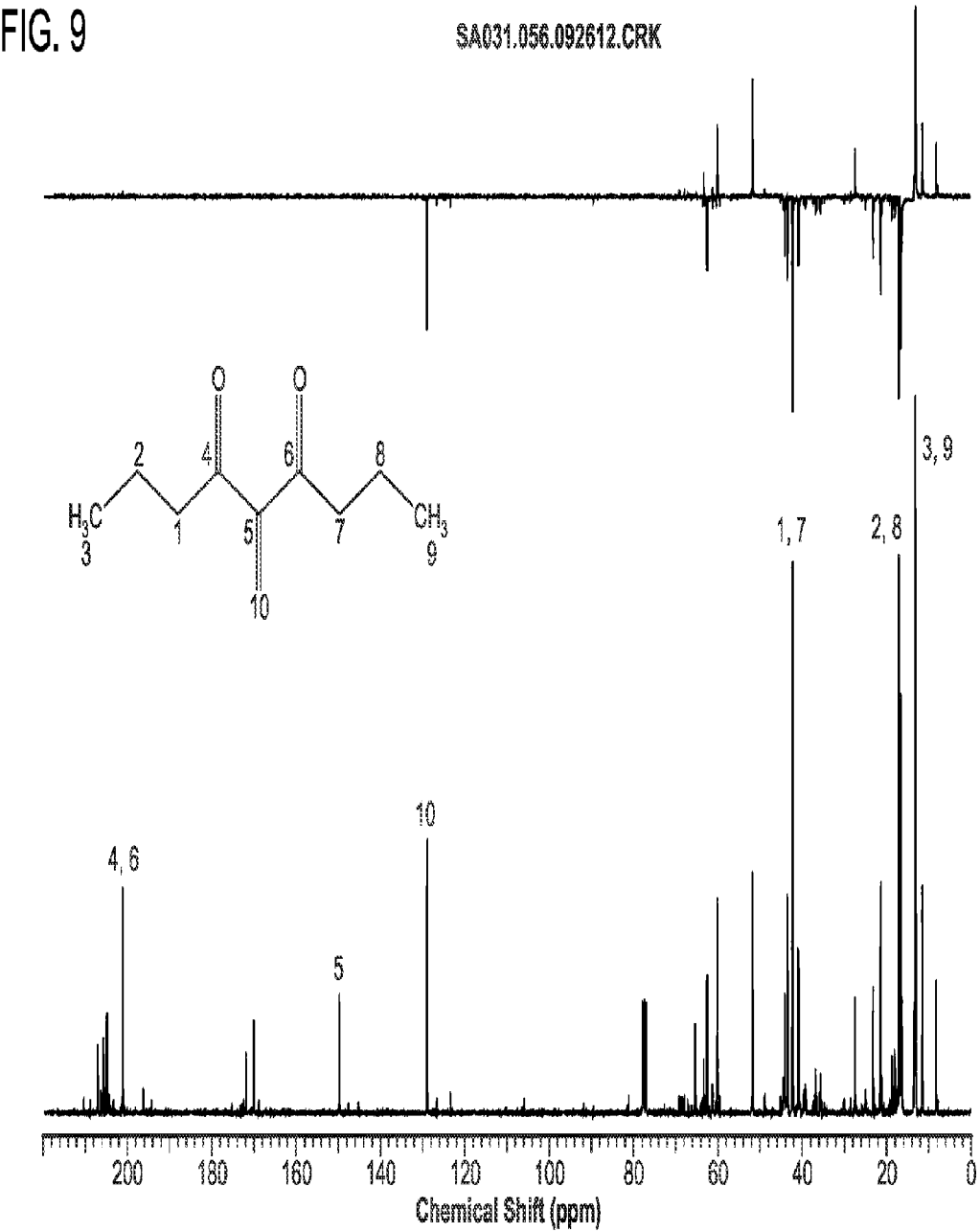

The $^1$H NMR spectrum is shown in FIG. 8. The peak at 6.2 ppm is consistent with the geminal double bond of the product. The 13C and DEPT-135 spectra are shown in FIG. 9. The peak at 129 ppm (CH$_2$) and at 150 ppm (quaternary) are consistent with the geminal double bond of the product.

Example 7

Additional Examples

The reaction scheme disclosed herein is performed using an appropriate 1,3-disubstituted-propane-1,3-dione and a source formaldehyde to obtain the following monomers.

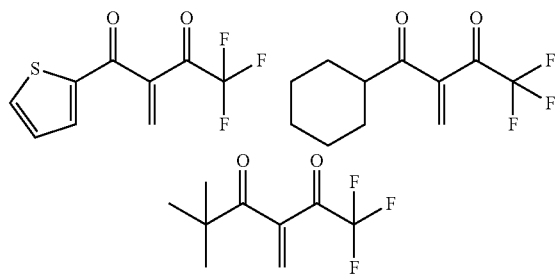

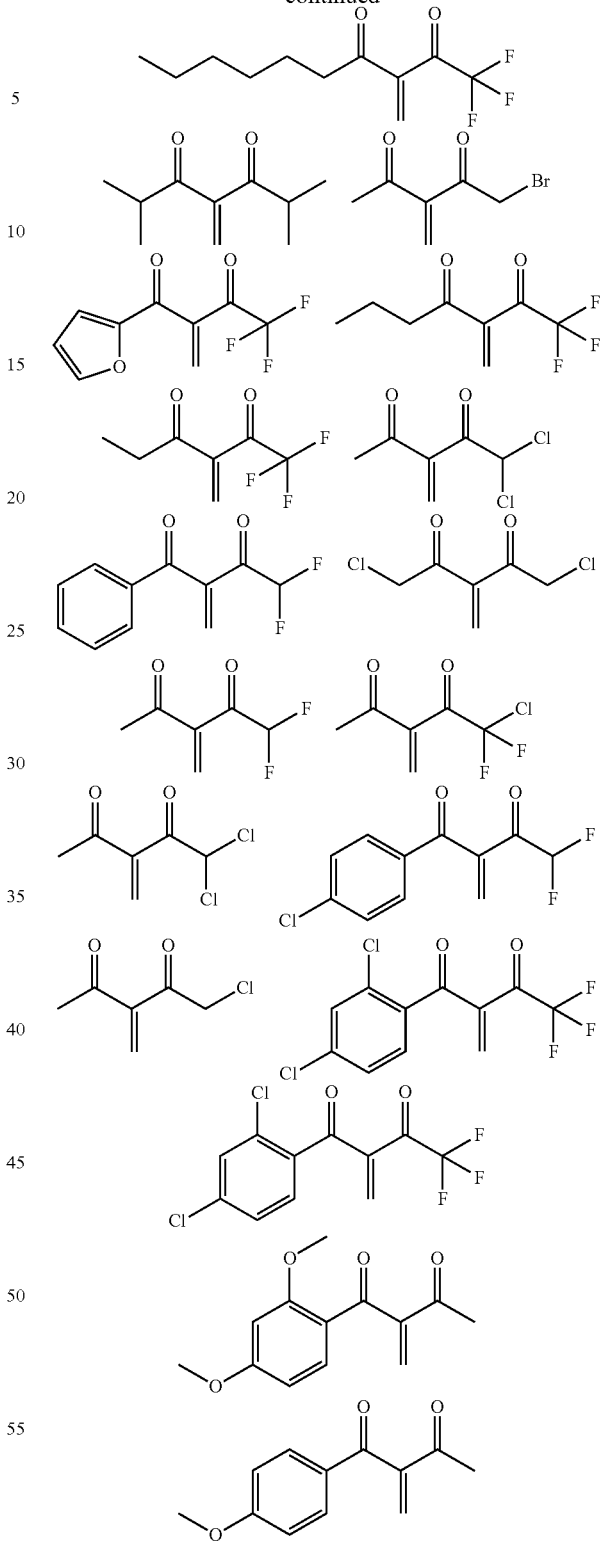

Equivalents

Those skilled in the art will recognize, or be able to ascertain using no more than routine experimentation, many equivalents to the specific embodiments of the invention described herein. Such equivalents are intended to be encompassed by this invention.

What is claimed is:

1. A methylene beta-diketone monomer having a structural formula selected from the group consisting of:

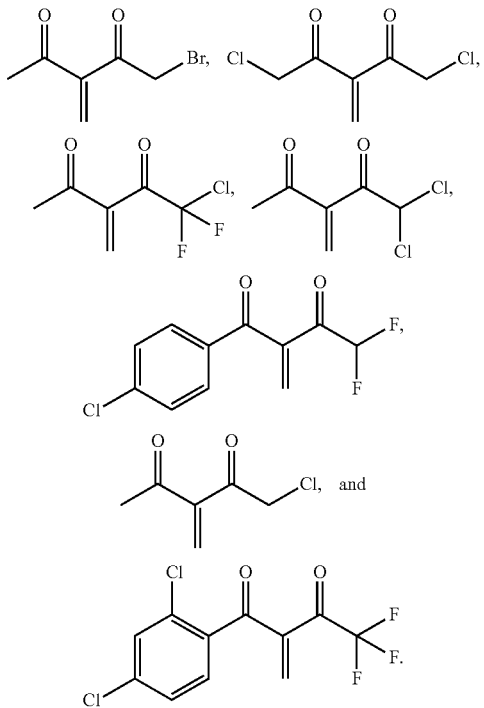

2. The monomer of claim 1, wherein the methylene beta-diketone monomer has the structural formula:

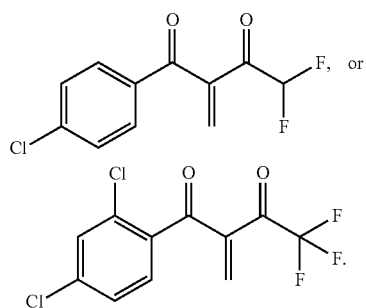

3. The monomer of claim 1, wherein the monomer has the structural formula selected from the group consisting of:

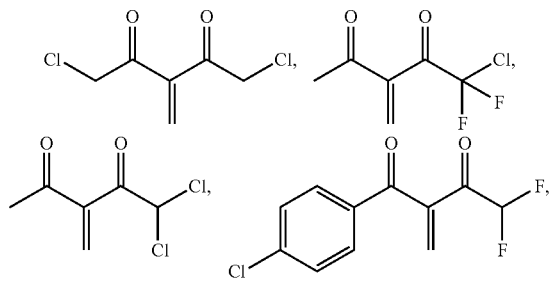

-continued

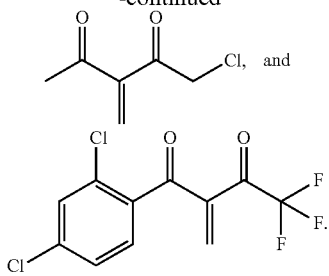

4. The monomer of claim 1, wherein the monomer has the structural formula selected from the group consisting of:

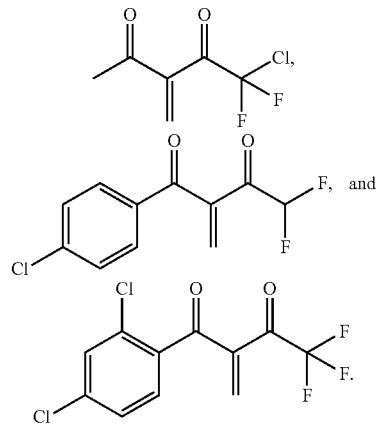

5. The monomer of claim 1, wherein the monomer has the structural formula

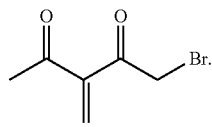

6. A polymerizable composition including at least one methylene beta-diketone monomer according to claim 1.

7. The polymerizable composition according to claim 6 further comprising a stabilizing amount of at least one stabilizer selected from the group consisting of: an acidic stabilizer, a vapor phase stabilizer, and a free radical stabilizer.

8. The polymerizable composition according to claim 7 wherein the at least one stabilizer includes the acidic stabilizer selected from trifluoromethane sulfonic acid, maleic acid, methane sulfonic acid, difluoro acetic acid, trichloroacetic acid, phosphoric acid, dichloroacetic acid, and chlorodifluoro acid.

9. The polymerizable composition according to claim 7 wherein the at least one stabilizer includes the vapor phase stabilizer selected from hydroquinone, methyl hydroquinone, butylated hydroxytoluene, butylated hydroxyanisole.

10. The methylene beta-diketone monomer according to claim 1 being formed as a reaction product of a 1,3-disubstituted-propane-1,3-dione represented by a structural formula selected from the group consisting of:

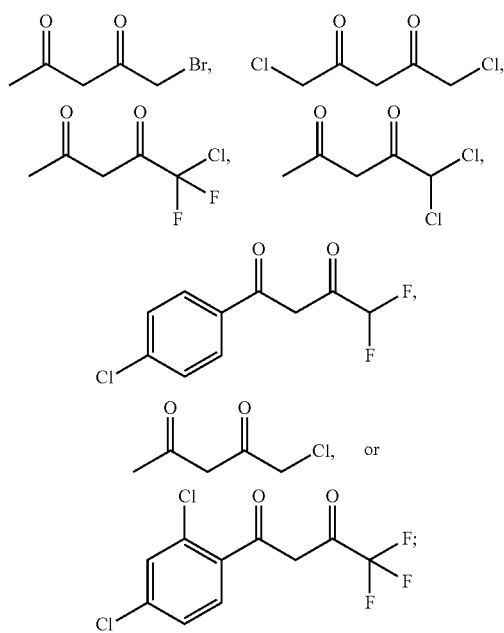

and a source of formaldehyde.

11. A method of preparing a methylene beta-diketone monomer comprising:

a) reacting a beta-diketone reactant having the structural formula selected from the group consisting of:

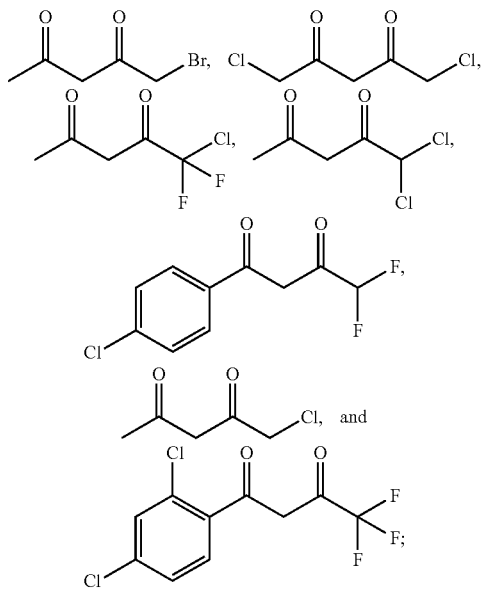

with a source of formaldehyde, optionally in the presence of an acidic or basic catalyst, and optionally in the presence of an acidic or non-acidic solvent, to form a reaction complex; and b) isolating a methylene beta-diketone monomer from the reaction complex, wherein the methylene beta-diketone monomer has the structural formula selected from the group consisting of:

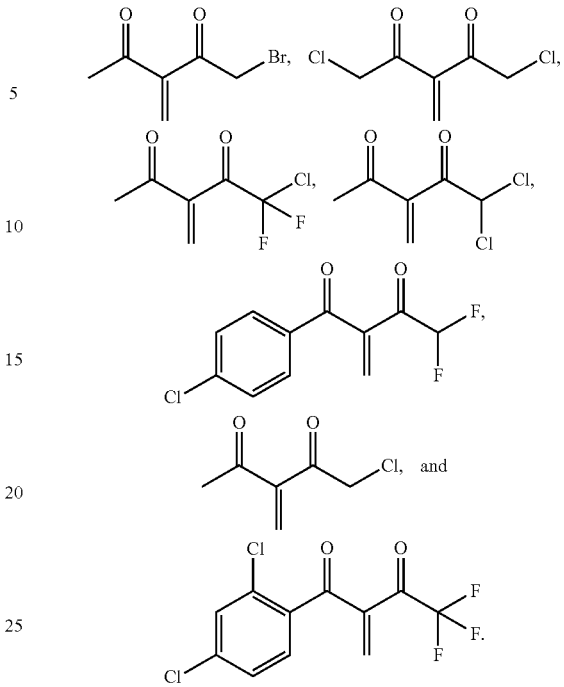

12. The method according to claim 11 wherein in step (b), isolating the methylene beta-diketone monomer comprises:

i. contacting the reaction complex, or a portion thereof, with an energy transfer means to produce a vapor phase including the methylene beta-diketone monomer; and ii. collecting the methylene beta-diketone monomer from the vapor phase.

13. The method of claim 11, wherein in step (b), isolating the methylene beta-diketone monomer comprises:

i. heating the reaction complex, or a portion thereof, to a temperature between about 130° C. and about 300° C. to produce a vapor phase including the methylene beta-diketone monomer; and ii. collecting the methylene beta-diketone monomer from the vapor phase.

14. The method according to claim 11 wherein the reaction conditions include:

a) an initiating temperature of between about 60° C. and about 130° C.; and b) atmospheric pressure.

15. A polymer having repeat units of the formula selected from the group consisting of:

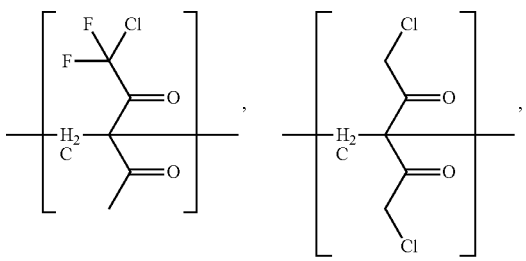

-continued

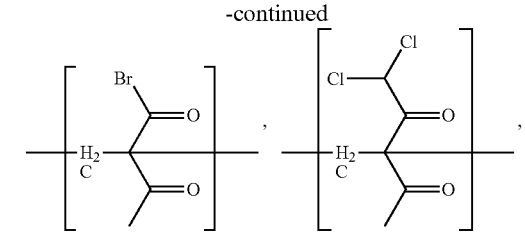

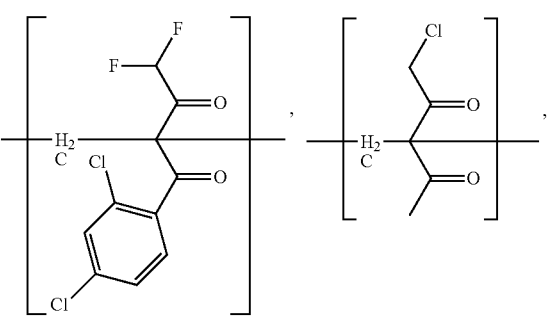

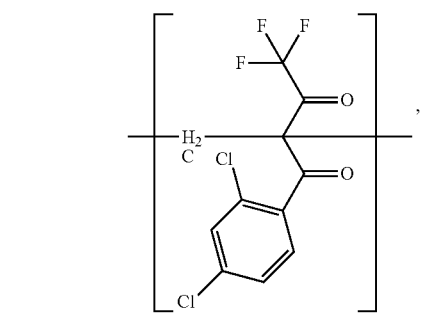

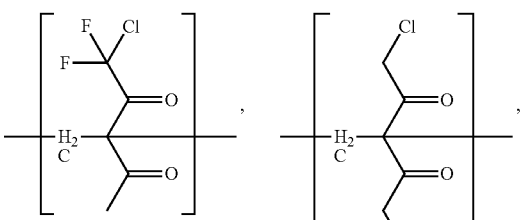

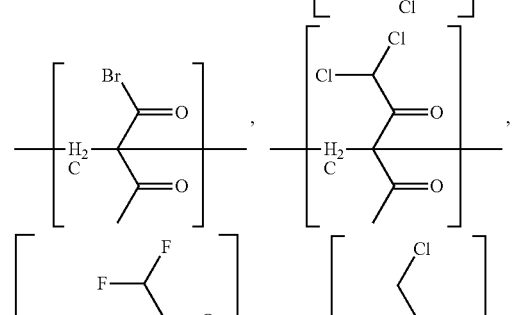

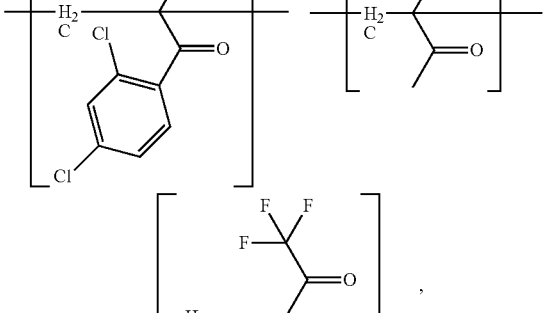

and combinations thereof.

16. An oligomeric complex prepared by reacting a beta-diketone reactant with a source of formaldehyde; optionally in the presence of heat transfer agent; optionally in the presence of an acidic or basic catalyst; and optionally in the presence of an acidic or non-acidic solvent, the oligomeric complex having between 2 and 12 repeat units having the structural formula selected from the group consisting of:

and combinations thereof.

* * * * *